United States Patent [19]

Tang et al.

[11] Patent Number: 5,508,387
[45] Date of Patent: Apr. 16, 1996

[54] SELECTIN BINDING GLYCOPEPTIDES

[75] Inventors: Peng C. Tang, Moraga; Daniel E. Levy; Kevin R. Holme, both of Alameda; Saeed A. Abbas, Vallejo, all of Calif.

[73] Assignee: Glycomed Incorporated, Alameda, Calif.

[21] Appl. No.: 102,032

[22] Filed: Aug. 4, 1993

[51] Int. Cl.$^6$ .................................................. C07K 17/10
[52] U.S. Cl. .......................... 530/403; 530/322; 536/53; 536/54; 536/18.7; 536/115
[58] Field of Search .................................... 530/322, 403; 536/53, 54, 18.7, 115

[56] References Cited

U.S. PATENT DOCUMENTS

| | | | |
|---|---|---|---|
| 4,386,026 | 5/1983 | Ponpipom et al. | 260/112.5 |
| 4,849,513 | 7/1989 | Smith et al. | 536/27 |
| 5,143,712 | 9/1992 | Brandley et al. | 424/1.1 |

FOREIGN PATENT DOCUMENTS

| | | |
|---|---|---|
| 0010405 | 4/1980 | European Pat. Off. . |
| 0063373 | 10/1982 | European Pat. Off. . |
| 0117648 | 9/1984 | European Pat. Off. . |
| 0501250 | 9/1990 | European Pat. Off. . |
| 0472220 | 2/1992 | European Pat. Off. . |
| 0020149 | 2/1985 | Japan . |
| 8802756 | 4/1988 | WIPO . |
| WO90/13300 | 11/1990 | WIPO . |

OTHER PUBLICATIONS

Osband et al., Immunology Today, vol. 11(6), 1990, pp. 193–195.
Waldmann, Science, vol. 252, pp. 1657–1662, 1991.
Liener et al., entitled "The Lectins: Properties, Functions and Applications in Biology and Medicine" published by *Academia* (1986).
Brandley et al., entitled "Cell–Surface Carbohydrates in Cell Recognition and Response" published by *J. Leuk Biology* 40:97–111 (1986).
Sharon et al., entitled "Lectins as Cell Recognition Molecules" published by *Science* 246:227–234 (1989).
Springer et al., published by *Nature* 346:425 (1990).
Stoolman et al., published by *Cell* 56:907 (1986).
Stoolman et al., entitled "Possible Role for Cell–Surface Carbohydrate–Binding Molecules in Lymphocyte Recirculation" published by *The Journal of Cell Biology* 96:722–727 (1983).
Fukuda et al., entitled "Structure of a Novel Sialylated Fucosyl Lacto–N–nor– hexaosylceramide Isolated from Chronic Myelogenous Leukemia Cells" published by *J. Biol. Chem.* 261:2376–2383 (1986).
Magnani et al., entitled "A Monoclonal Antibody–defined Antigen Associated with Gastrointestinal Cancer is a Ganglioside Containing Sialylated Lacto–N–fucopentaose II" published by *J. Biol Chem.* 257:14365–14369 (1982).
Hakomori et al., entitled "Human Cancer–Associated Gangliosides Defined by a Monoclonal Antibody (IB9) Directed to Sialosylα2→6 Galactosyl Residue: A Preliminary Note" published by *Biochem. Biophys. Res. Comm.* 113:791–798 (1983).
Fukushi et al., entitled "Localization and Alteration of Mono–, DI–, and Trifucosyl α1→3 Type 2 Chain Structures During Human Embryogenesis and in Human Cancer" published by *J. Exp. Med.* 159:506–520 (1984).
Gong et al., published by *Nature* 343:757 (1990).
Geoffroy et al., entitled "Demonstration that a Lectin–like Receptor (gp90$^{MEL}$) Directly Mediates Adhesion of Lymphocytes to High Endothelial Venules of Lymph Nodes" published by *J Cell Biol.* 109:2463–2469 (1989).
Lasky et al., entitled "Cloning of a Lymphocyte Homing Receptor Reveals a Lectin Domain" published by *Cell* 56:1045–1055 (1989).
Oldenburg et al., entitled "Peptide Ligands for a Sugar–Binding Protein Isolated from a Random Peptide Library" published by *Proc. Natl. Acad. Sci.* 89:5393–5397 (1992).
Tyrell et al. published by *Proc. Natl. Acad. Sci. USA* 88:10372 (1991).
Berg et al., published by *J Biol. Chem* 265:14869 (1991).
Handa et al., published by *Biochem Biophys Res Commun* 181:1223 (1991).
Foxall et al., entitled "The Three Members of the Selectin Receptor Family Recognize a Common Carbohydrate Epitope, the Sialyl Lewis$^x$ Oligosaccharide" published by *The Journal of Cell Biology* 117:895–902 (1992).
Aruffo et al., published by *Proc Natl Acad Sci USA* 84:8573 (1987).
Polte et al., published by *Nucleic Acids Res* 18:1083 (1990).
Hession et al., published by *Proc Natl Acad Sci USA* 87:1673 (1990).
Blackburn et al., published by *J. Biol. Chem* 261:2873 (1986).
Carlson et al, entitled "A Greatly Improved Procedure for Ruthenium Tetraoxide Catalyzed Oxidations of Organic Compounds" published by *J. Org. Chem* 46:3936–3937 (1981).
Green et al., entitled "Preparation of Pentafluorophenyl Esters of FMOC Protected Amino Acids with Pentafluorophenyl Trifluoroacetate" published by *Tetrahedron Letters* 31:5851–5852 (1990).
Coste et al., published by *Tetrahedron Letters* 31:205 (1990).
Arnaout et al., published by *Blood* 75:1037 (1990).
Bevilacqua et al., entitled "Identification of an Inducible Endothelial–Leukocyte Adhesion Molecule" published by *Proc Natl. Acad. Sci. USA* 84:9238–1942 (1987).

(List continued on next page.)

Primary Examiner—Michael G. Wityshyn
Assistant Examiner—C. Sayala
Attorney, Agent, or Firm—Lyon & Lyon

[57] ABSTRACT

Glyco-amino acids or glycopeptides that have three-dimensionally stable configuration for the presentation of functional groups, fucose, or an analogue or derivative thereof, covalently linked to an amino acid or peptide with a free carboxylic acid group, that facilitate binding between those groups and receptors on selectins, represented by the general structural formula I.

8 Claims, 5 Drawing Sheets

OTHER PUBLICATIONS

Bevilacqua et al., entitled "Endothelial Leukocyte Adhesion Molecule 1: An Inducible Receptor for Neutrophils Related to Complement Regulatory Proteins and Lectins" published by *Science* 243:1160–1165 (1989).

Larsen et al., published by *Cell* 59:305 (1989).

Lo et al., published by *J. Immunol.* 143:3325 (1989).

Lowe et al., entitled "ELAM–1–Dependent Cell Adhesion to Vascular Endothelium Determined by a Transfected Human Fucosyltransferase cDNA" published by *Cell* 63:475–484 (1990).

Phillips et al., published by *Science* 250:1130 (1990).

Spertini et al., entitled "Regulation of Leukocyte Migration by Activation of the Leukocyte Adhesion Molecule–1 (LAM–1) Selectin" published by *Nature* 349:691–694 (1991).

Swank–Hill et al. published by *Anal.Biochem* 183:27 (1987).

Walz et al., published by *Science* 250:1132 (1990).

Watson et al., entitled "Neutrophil Influx into an Inflammatory Site Inhibited by a Soluble Homing Receptor–IgG Chimaera" published by *Nature* 349:164–167 (1991).

Bevilacqua et al., entitled "Selectins" published by *J. Clin Invest.* 91:379–387 (1993).

1 - N-[(1-deoxy-α-L-fucopyranosyl)acetyl]-L-proline-L-phenylalanine

2 - N-[(1-deoxy-α-L-fucopyranosyl)-L-alanine-L-proline-L-phenylalanine

3 - N-ω-t-butoxylcarbonyl-N-α-[(1-deoxy-α-L-fucopyranosyl)acetyl]-L-lysine

4 - N-[4-(1-deoxy-α-L-fucopyranosyl)n-butanoyl]-L-proline-L-phenylalanine

5 - N-[(1-deoxy-α-L-fucopyranosyl)acetyl]-L-proline-L-phenylglycine

6 - N-[4-(deoxy-α-L-fucopyranolsyl)n-butanoyl]-L-phenylalanine

1 - N-[(1-deoxy-α-L-fucopyranosyl)acetyl]-L-proline-L-phenylalanine

2 - N-[(1-deoxy-α-L-fucopyranosyl)-L-alanine-L-proline-L-phenylalanine

3 - N-ω-t-butoxylcarbonyl-N-α-[(1-deoxy-α-L-fucopyranosyl)acetyl]-L-lysine

4 - N-[4-(1-deoxy-α-L-fucopyranosyl)n-butanoyl]-L-proline-L-phenylalanine

5 - N-[(1-deoxy-α-L-fucopyranosyl)acetyl]-L-proline-L-phenylglycine

6 - N-[4-(deoxy-α-L-fucopyranolsyl)n-butanoyl]-L-phenylalanine

1 - N-[(1-deoxy-α-L-fucopyranosyl)acetyl]-L-proline-L-phenylalanine
2 - N-[(1-deoxy-α-L-fucopyranosyl)-L-alanine-L-proline-L-phenylalanine

1 - N-[(1-deoxy-α-L-fucopyranosyl)acetyl]-L-proline-L-phenylalanine

2 - N-[(1-deoxy-α-L-fucopyranosyl)-L-alanine-L-proline-L-phenylalanine

3 - N-ω-t-butoxylcarbonyl-N-α-[(1-deoxy-α-L-fucopyranosyl)acetyl]-L-lysine

4 - N-[4-(1-deoxy-α-L-fucopyranosyl)n-butanoyl]-L-proline-L-phenylalanine

5 - N-[(1-deoxy-α-L-fucopyranosyl)acetyl]-L-proline-L-phenylglycine

SELECTIN BINDING GLYCOPEPTIDES

FIELD OF THE INVENTION

This invention relates generally to medicinal chemistry, and preferably to methods of synthesizing and identifying medically useful glyco-amino acids or glycopeptides which are characterized by their capacity to bind to one or more selectins (E-, L-, and P-selectins).

BACKGROUND OF THE INVENTION

Carbohydrate-protein interactions form the basis of a host of biological processes (Clarke A. E. & Wilson I. A., eds. (1988), *Carbohydrate-protein interactions* (Springer, Heidelberg); and Liener et al (1986) *The Lectins: Properties, Functions and Applications in Biology and Medicine* (Academia, Orlando, Fla.)). The role of carbohydrates in physiologically relevant recognition has been widely considered (Brandley et al., *J Leuk Biol* (1986) 40:97; and Sharon et al., *Science* (1989) 246:227). For example, the cell-surface mediates such processes as cell-cell adhesion (Springer et al, *Nature* (1990) 346:425) and lymphocyte adhesion through lymphoid tissues (Stoolman, L. M., *Cell* (1986) 56: 907). Carbohydrate recognition is central to the enzymatic synthesis and degradation of polysaccharides, glycoproteins and glycolipids that play essential roles in metabolism and maintenance of cellular structures.

Tumor associated glycolipids have been reported in fetal tissue and a variety of human cancers, including CML cells (Fukuda et al., *J Biol Chem* (1986) 261:2376; Magnani et al., *J Biol Chem* (1982) 257:14365; Hakomori et al., *Biochem Biophys Res Comm* (1983) 113:791). This has led to the hypothesis that these structures may be important in many developmental and oncogenic processes (Magnani et al., *J Biol Chem* (1982) 257:14365). Smaller quantities of most of these carbohydrates can be found in normal human tissue (see Fukushi et al., *J Exp Med* (1984) 160:506), but until now no function for these structures has been reported.

Adhesion of circulating neutrophils to stimulated vascular endothelium is a primary event of the inflammatory response. Several receptors have been implicated in this interaction, including a family of putative lectins that includes L-selectin (gp90$^{MEL}$, Leu8), P-selectin (GMP-140, PADGEM) and E-selectin (ELAM-1) (Gong et al., *Nature* (1990) 343:757; Johnston et al., *Cell* (1989) 56:1033; Geoffrey et al., *J Cell Biol* (1989) 109:2463; Lasky et al., *Cell* (1989) 56:1045). These receptors each contain a domain with sequence homology to calcium dependent lectins. The receptor gp90$^{MEL}$ has been demonstrated to recognize a carbohydrate (See Geoffrey et al., *J Cell Biol* (1989) 109:2463). Endogenous ligands for these receptors are beginning to be characterized (see U.S. Pat. No. 5,143,712 issued Sep. 1, 1992, incorporated herein by reference).

E-selectin or ELAM-1 is particularly interesting because of its transient expression on endothelial cells in response to IL-1 or TNF (Bevilacqua et al., *Science* (1989) 243:1160). The time course of this induced expression (2–8 h) suggests a role for this receptor in initial neutrophil extravasation in response to infection and injury. Furthermore, Bevilacqua et al (Bevilacqua et al., *Proc Natl Acad Sci USA* (1987) 84:9238) have demonstrated that human neutrophils or HL-60 cells will adhere to COS cells transfected with a plasmid containing a cDNA encoding for the ELAM-1 receptor.

Several different groups have published papers regarding ELAM-1 ligands which ligands are also referred to as LECAM-2 ligands. Lowe et al (1990) demonstrated a positive correlation between the LECAM-2 dependent adhesion of HL-60 cell variants and transfected cell lines, with their expression of the sialyl Lewis x (sLe$^x$) oligosaccharide, Neu NAc α2-3Gal-β1-4(Fuc α1-3)-GlcNAc. They concluded that one or more members of a family of oligosaccharides consisting of sialylated, fucosylated, lactosaminoglycans are the ligands for the lectin domain of LECAM-2. Phillips et al (1990) used antibodies with reported specificity for sLe$^x$ to inhibit the LECAM-2 dependent adhesion of HL-60 or LEC11 CHO cells to activated endothelial cells. Liposomes containing difucosylated glycolipids with terminal sLe$^x$ structures inhibited adhesion, while those containing non-sialylated Le$^x$ structures were partially inhibitory. Walz et al (1990) were able to inhibit the binding of a LECAM-2-1gG chimera to HL-60 cells with a monoclonal antibody directed against sLe$^x$ or by glycoproteins with the sLe$^x$ structure, but could not demonstrate inhibition with CD65 or CD15 antibodies. Both groups concluded that the sLe$^x$ structure is the ligand for LECAM-2.

P-selectin expressed on activated platelets mediates binding to multiple leukocyte types (Bevilacqua et al, *J. Clin. Invest.* (1993) 91:379). Endothelial P-selectin also supports leukocyte adhesion.

LECAM-1 is particularly interesting because of its ability to block neutrophil influx (Watson et al., *Nature* (1991) 349:164–167). It was expressed in chronic lymphocytic leukemia cells which bind to HEV (see Spertini et al., *Nature* (1991) 349:691–694).

It is believed that HEV structures at sites of chronic inflammation are associated with the symptoms of disease such as rheumatoid arthritis, psoriasis, and multiple sclerosis.

Information regarding the DNA sequences encoding endothelial cell-leukocyte adhesion molecules are disclosed in PCT published application WO90/13300 published Nov. 15, 1990 incorporated herein by reference. The PCT publication cites numerous articles which may be related to endothelial cell-leukocyte adhesion molecules. The PCT publication claims methods of identifying ELAM-ligands, as well as methods of inhibiting adhesion between leukocytes and endothelial cells using such ligands and specifically refers to MILAs which are described as molecules involved in leukocyte adhesion to endothelial cells.

In general, the above publications are directed toward identifying and characterizing endogenous ligands which are carbohydrates.

The development of potent inhibitors of carbohydrate-specific proteins would be of considerable importance in the generation of new therapeutic agents. Oligosaccharides are well positioned to act as recognition molecules due to their cell surface location and structural diversity. However, these carbohydrates are very complex in nature and are expensive and time consuming to synthesize. Chemical synthesis of oligosaccharides requires sophisticated strategies that control product stereochemistry and regiochemistry. Enzymatic synthesis using glycosyltransferases, a viable alternative to chemical synthesis, is limited by the availability of enzymes with appropriate specificities.

Peptides have been suggested as an alternative approach to the synthesis of polysaccharide ligands for carbohydrate-specific receptors (Oldenburg et al, *Proc. Natl. Acad. Sci.* (1992) 89:5393).

Cell-specific glycopeptide ligands coupled to bioactive materials have been used as a means to deliver said bioactive materials to the selected site (see European Patent Application, Publication No. 63373, published Oct. 27, 1982; and U.S. Pat. No. 4,386,026 issued May 31, 1983 incorporated herein by reference).

SUMMARY OF THE INVENTION

A primary object of the invention is to provide medically useful glyco-amino acids or glycopeptides (herein also referred to as compounds) that are characterized by their capacity to bind to certain selectins, and that are cost-effective to synthesize.

A second object of the invention is the description of certain glyco-amino acids or glycopeptides that bind to certain selectins, that is have selectin ligand activity, and consist of fucose, or an analogue or derivative thereof, attached to an amino acid or a peptide having a free carboxylic acid group. Relative to sLe$^x$, a known selectin ligand, the invention glyco-amino acids or glycopeptides are cost-effective to synthesize.

A third object of the present invention is a description of the design and synthesis of glyco-amino acids or glycopeptides that have three-dimensionally stable configurations for the presentation of certain functional groups, a charged group, preferably a carboxylic acid or a sulfate group, and fucose, or analogues or derivatives thereof, such that fucose is covalently linked to an amino acid or a peptide with a free carboxylic acid group, and such that the orientation of the functional groups facilitate binding between those groups and certain selectins.

Such invention glyco-amino acids or glycopeptides are represented by the following general structural formula I:

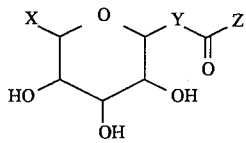

wherein
m and u are integers of from 1 or 2; p, q and w are integers of from 1 to 6; r and s are integers of from 0 or 1; and t is an integer of from 0 to 3;
and
A is —COOH or —CH$_2$OSO$_3$H;
B is —R$^1$, —CH(R$^1$)$_2$, —CH$_2$OCH$_2$R$^1$ or —CH$_2$SCH$_2$R$^1$;
D is —L$^1$—[(CH$_2$)$_w$—M]$_r$ or —L$^2$—[(CH$_2$)$_w$—M]$_r$;
E is H or —(CH$_2$)$_w$—[K—(CH$_2$)$_q$]$_r$—M$^1$ with the proviso that either G is H or M$^2$ is H, when E is —(CH$_2$)$_w$—[K—(CH$_2$)$_q$]$_r$—M$^1$;
G is H or —[K—(CH$_2$)$_q$]$_r$—M$^2$ with the proviso that either E is H or M$^1$ is H when G is —[K—(CH$_2$)$_q$]$_r$—M$^2$;
J is —SO$_2$— when D is —L$^1$—[(CH$_2$)$_w$—M]$_r$; or
J is —CO— or —CS— when D is —L$^2$—[(CH$_2$)$_w$—M]$_r$;
K is —O—, —S—, —NH—, —S—S—, —CO—, —CONH—;
L$^1$ is —NH—, —CH$_2$—, —NHR$^1$ or —R$^4$ with the proviso that L$^1$ is either R$^4$ or —NHR$^1$ when r is 0;
L$^2$ is —O—, —S—, —NH—, —CH$_2$—, —OR$^4$, —SR$^4$, —NHR$^1$ or —R$^4$ with the proviso that L$^2$ is either —OR$^4$, —SR$^4$, —NHR$^1$ or —R$^4$ when r is 0;
M, M$^1$ and M$^2$ are independently H or —[CO—Q]$_s$ Q is a carrier moiety to obtain multivalent compounds, the carrier moieties selected from the group of amines such as —N(CH$_2$CH$_2$NH—)$_3$, proteins and peptides;
X is —R$^2$, —OR$^2$ or —CH$_2$OR$^2$;
Y is —(CHR$^3$)$_t$— with the proviso that there are no more than two OH groups; or
—O—(CHR$^3$)$_u$— with the proviso that there is no more than one OH group;
wherein
R$^1$ and R$^2$ are independently H, an alkyl group containing 1 to 6 carbon atoms, aryl group or an arylalkyl group;
R$^3$ is H or OH;
R$^4$ is an alkyl group containing 1 to 6 carbon atoms, aryl group or an arylalkyl group.

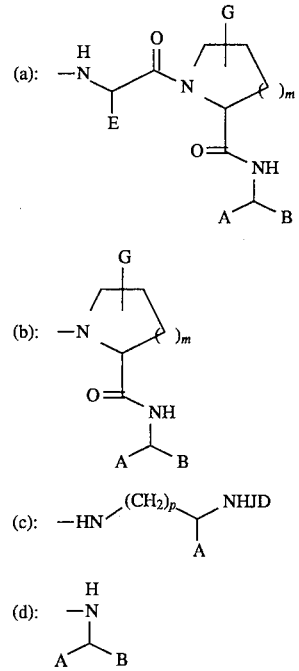

The glyco-amino acids or glycopeptides may be in the form of a prodrug or in the form of multivalent derivatives of compounds of structural formula I.

A fourth object of the invention is to provide a description of methods to treat or diagnose disease using glyco-amino acids or glycopeptides.

A fifth object of the invention is to provide a composition comprising a glyco-amino acid or glycopeptide of the current invention bound to a detectable label and/or bound to a pharmaceutically active drug such as an anti-inflammatory drug.

A sixth object of the invention is to provide a pharmaceutical formulation containing a glyco-amino acid or glycopeptide of the current invention which is useful for treating or diagnosing certain diseases.

A seventh object of the invention is to provide a pharmaceutical formulation containing a glyco-amino acid or glycopeptide of the invention which is useful for treating inflammation.

An eighth object of the invention includes providing methods to treat inflammation and to determine the site of inflammation by administering formulations of the type referred to above.

Another object is to provide a pharmaceutical formulation containing a glyco-amino acid or glycopeptide of the current invention which is useful for treating cancer.

These and other objects, advantages and features of the present invention will become apparent to those persons skilled in the art upon reading the details of the isolation, structure, formulation and usage as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying figures as follows.

DETAILED DESCRIPTION OF THE INVENTION

Figure 1:
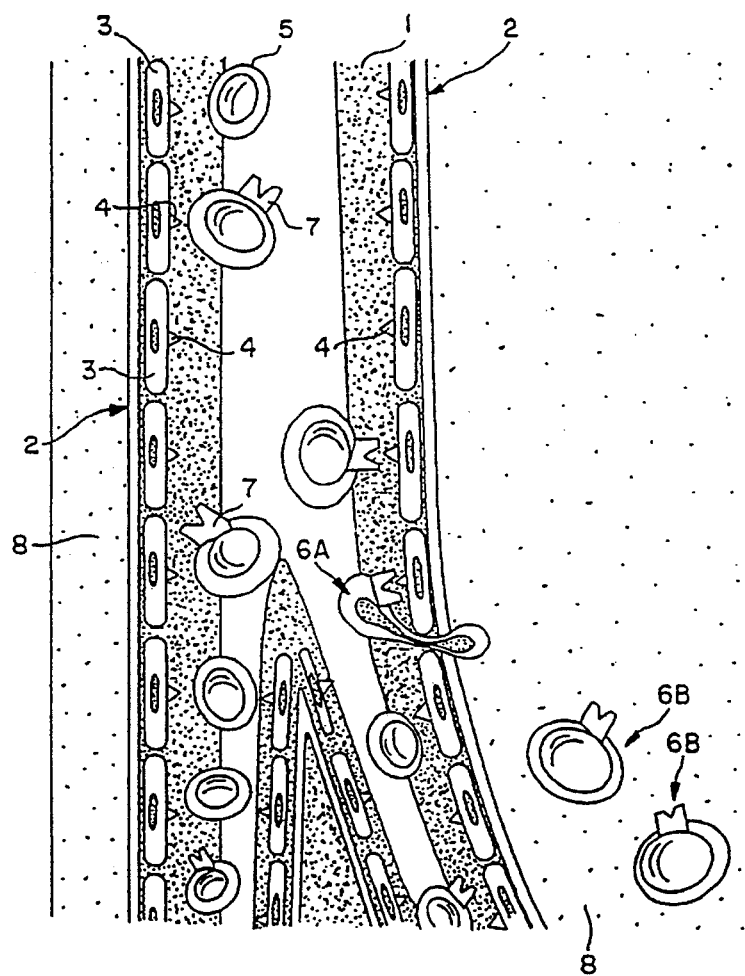
FIG. 1 is a cross-sectional schematic view showing the interaction between white blood cells and activated endothelial cells.

As used in this specification and the appended claims, the singular forms "a", "an" and "the" include plural referents unless the context clearly dictates otherwise. Thus, for example, reference to "a glyco-amino acid or glycopeptide" includes mixtures of such compounds, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth. A prodrug is defined as a protected compound wherein the active form of the compound is released within the body of the patient as a result of hydrolysis by enzymes such as esterases. All publications mentioned herein are incorporated by reference.

Some standard abbreviations used in connection with the present invention include: BSA, bovine serum albumin; DEAE, diethylaminoethyl; DMSO, dimethyl-sulfoxide; ELAM-1, endothelial/leukocyte adhesion molecule-1; HPTLC, high performance thin layer chromatography; LECAM-1, leukocyte/endothelial cell adhesion molecule-1; PVC, polyvinylchloride; TLC, thin layer chromatography; TFA, trifluoroacetic acid; Tris, tris (hydroxymethyl) aminomethane; BSA, bovine serum albumin; TBS, tris buffered saline; DMF, dimethylformamide; Ab-AP, antibody to alkaline phosphatase; Ac, acetate; Bn, benzyl.

Development of the Invention

ELAM-1 has a lectin like domain that recognizes sialyl Lewis (sLe$^x$) tetrasaccharide as shown below in structural formula II.

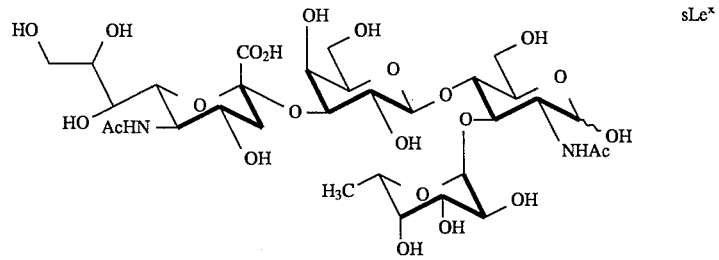

The ability of SLe$^x$ to bind ELAM-1 is described by Lowe et al., Cell (1990) 63:475; Phillips et al., Science (1990) 2:50:1130; Walz et al., Science (1990) 250:1132; and Tyrell et al., Proc. Natl. Acad. Sci. USA (1991) 88:10372.

It has also been shown (Berg et al., J Biol Chem (1991) 265:14869; Handa et al., Biochem Biophys Res Commun (1991) 181:1223) that both ELAM-1, and GMP-140, also known as P-selectin, recognize the isomeric tetrasaccharide sLe$^a$, as shown below in the structural formula III.

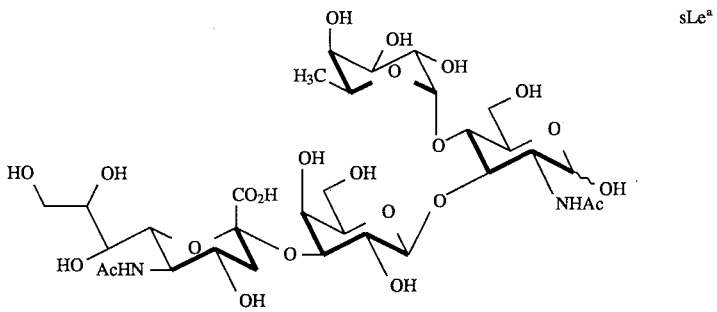

sLe$^a$

A structural examination of sLe$^x$ or sLe$^a$ indicates that they share a structural similarity in three dimensional arrangement. Specifically, the sialic acid and fucose rings are similarly oriented in space in a manner suitable for recognition by the selectins.

Amino acids and peptides consist of a carboxyl terminal and an amino terminal. We theorized that we could use a carboxyl terminal of an amino acid or peptide to replace the carboxylic acid group of sialic acid associated with sLe$^x$, and to further mimic sLe$^x$, we thought to attach fucose, or an analogue or derivative thereof, at the N-terminal end of an amino acid or peptide. Linking the fucose to an amino acid or peptide tremendously simplifies the synthesis of these glyco-amino acids or glycopeptides.

One face of galactose of sLe$^x$ is lipophilic, and we believe this is involved in binding to the selectins. Thus, we further theorized that by replacing the galactose associated with sLe$^x$, with a lipophilic or aromatic amino acid, preferably phenylalanine, diphenylphenylalanine, tyrosine, methoxytyrosine, histidine or phenylglycine, we could better mimic sLe$^x$.

We deduced that the corresponding epitopes on the lectin domain of ELAM-1 and perhaps other selectins are spaced in a similar three-dimensional configuration such that attaching fucose, or an analogue or derivative thereof, to an amino acid or a peptide with a free carboxylic acid group, wherein the amino acid or the peptide preferably has a lipophilic or an aromatic amino acid, would yield active ligands that are markedly different from the natural ligand.

Following this hypothesis we have designed the simplest form of similar structures which bind to a selectin. This has been done by attaching L-fucose, or an analogue or derivative thereof, using peptide coupling methods to N-terminal amino acids or peptides with a free carboxylic acid acting as a sialic acid mimic to provide a series of glyco-amino acids or glycopeptides of structural formula I. This series of glyco-amino acids or glycopeptides is designed to competitively inhibit selectins from binding to their natural ligands. These glyco-amino acids or glycopeptides can be combined with pharmaceutically acceptable excipients to provide pharmaceutical compositions useful in a wide range of treatments.

The glyco-amino acids or glycopeptides that contain the appropriate reactive functions can be reacted with suitably protected hydrophobic carriers like ceramide or a ceramide mimic, steroids, diglycerides or phospholipids to form molecules that act as immunomodulators.

The glyco-amino acids or glycopeptides of the current invention can act as antagonist ligand molecules, i.e. biochemical blocking agents, by binding to selectins and preventing circulating neutrophils from binding to stimulated endothelial cells, thereby preventing a primary event involved in certain diseases, including the inflammatory response. Agonist ligands have the opposite effect.

The synthetic glyco-amino acids or glycopeptides of the present invention are designed to provide a three-dimensionally stable configuration for functional groups wherein ligands with fucose, or an analogue or derivative thereof, attached to the N-terminal amino acid or peptide with a free carboxyl group, so as to allow for binding between those groups and receptors on natural selectins. The glyco-amino acids or glycopeptides are represented by the following general structural formula I:

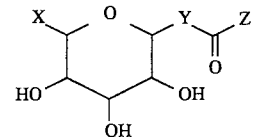

wherein m and u are integers of from 1 or 2; p, q and w are integers of from 1 to 6;

r and s are integers of from 0 or 1; and t is an integer of from 0 to 3;

and

A is —COOH or —CH$_2$OSO$_3$H;

B is —R$^1$, —CH(R$^1$)$_2$, —CH$_2$OCH$_2$R$^1$ or —CH$_2$SCH$_2$R$^1$;

D is —L$^1$—[(CH$_2$)$_w$—M]$_r$ or —L$^2$—[(CH$_2$)$_w$—M]$_r$;

E is H or —(CH$_2$)$_w$—[K—(CH$_2$)$_q$]$_r$—M$^1$ with the proviso that either G is H or M$^2$ is H, when E is —(CH$_2$)$_w$—[K—(CH$_2$)$_q$]$_r$—M$^1$;

G is H or —[K—(CH$_2$)$_q$]$_r$—M$^2$ with the proviso that either E is H or M$^1$ is H when G is —[K—(CH$_2$)$_q$]$_r$—M$^2$;

J is —SO$_2$— when D is —L$^1$—[(CH$_2$)$_w$—M]$_r$; or

J is —CO— or —CS— when D is —L$^2$—[(CH$_2$)$_w$—M]$_r$;

K is —O—, —S—, —NH—, —S—S—, —CO—, —CONH—;

L$^1$ is —NH—, —CH$_2$—, —NHR$^1$ or —R$^4$ with the proviso that L$^1$ is either R$^4$ or —NHR$^1$ when r is 0;

L$^2$ is —O—, —S—, —NH—, —CH$_2$—, —OR$^4$, —SR$^4$, —NHR$^1$ or —R$^4$ with the proviso that L$^2$ is either —OR$^4$, —SR$^4$, —NHR$^1$ or —R$^4$ when r is 0;

M, M$^1$ and M$^2$ are independently H or —[CO—Q]$_s$

Q is a carrier moiety to obtain multivalent compounds, the carrier moieties selected from the group of amines such as —N(CH$_2$CH$_2$NH—)$_3$, proteins and peptides;

X is —R$^2$, —OR$^2$ or —CH$_2$OR$^2$;

Y is —(CHR$^3$)$_t$— with the proviso that there are no more than two OH groups; or —O—(CHR$^3$)$_u$— with the proviso that there is no more than one OH group;

wherein

R$^1$ and R$^2$ are independently H, an alkyl group containing 1 to 6 carbon atoms, aryl group or an arylalkyl group preferably benzyl;

R$^3$ is H or OH;

R$^4$ is an alkyl group containing 1 to 6 carbon atoms, aryl group or an arylalkyl group.

Z is

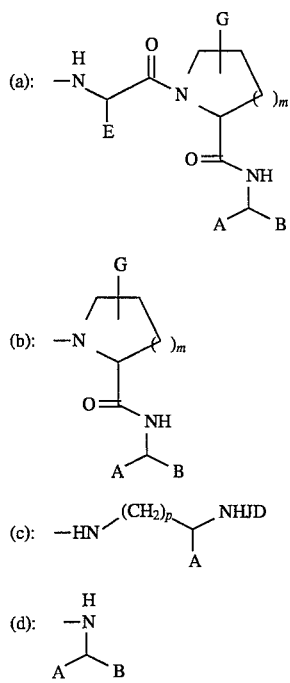

Referring now to FIG. 1, a cross-sectional view of a blood vessel 1 is shown. The vessel wall 2 is lined internally with endothelial cells 3. The endothelial cells 3 can be activated causing the cells 3 to synthesize ELAM-1 which is displayed in FIG. 1 as a triangular surface receptor 4. Both red blood cells 5 and white blood cells 6 flow in the vessel 1. The white blood cells 6 display carbohydrate ligands 7 which have chemical and physical characteristics which allow the ligands 7 to bind to the receptors 4. Once the ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation.

Figure 2:
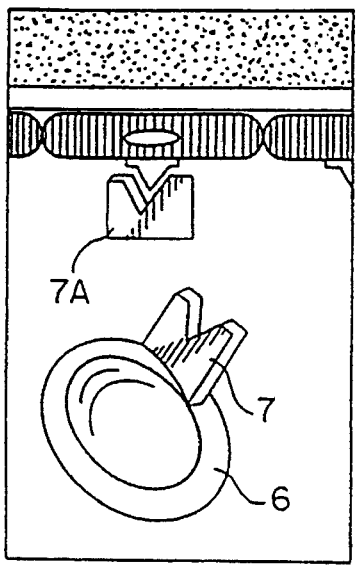
FIG. 2 is a cross-sectional schematic view showing how glyco-amino acids or glycopeptides of the invention might be used as pharmaceuticals to block ELAM-1.

An important aspect of the present invention can be described by referring to FIG. 2. The glyco-amino acids or glycopeptides of structural formula I are shown as 7A and can adhere to a selectin such as ELAM-1 by themselves and can be formulated into pharmaceutical compositions, which when administered, will effectively block the ELAM-1 and prevent the adhesion of a ligand 7 connected to a white blood cell 6. By administering pharmaceutically effective amounts of the glyco-amino acids or glycopeptides 7A, some, but not all, of the white blood cells will not reach the surrounding tissue 8. By slowing the rate at which the white blood cells reach the surrounding tissue, inflammation can be prevented and/or alleviated.

Figure 3:
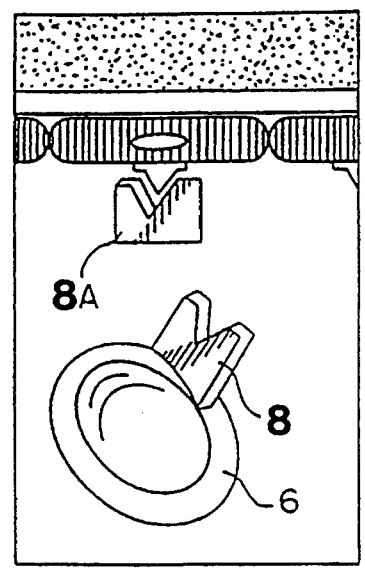
FIG. 3 is a cross-sectional schematic view showing how glyco-amino acids or glycopeptides of the invention might be used as pharmaceuticals to block LECAM-1.

Another important aspect of the invention can be described with reference to FIG. 3. In FIG. 3 the LECAM-1 receptor 8 on the white blood cell 6 is blocked by the glyco-amino acids or glycopeptides of formula I represented by 8A. The present inventors have found that a given glyco-amino acid or glycopeptide, 8A which presents hydrogen bond donor groups in a configuration as shown in structure I can block E-, L- and/or P-selectins.

It is known that for an acute inflammatory response to occur, circulating neutrophils must bind to and penetrate the vascular wall and access the site of injury. Several molecules have been implicated in this interaction, including a family of putative carbohydrate ligands and their receptors. One molecule that was previously identified is the endogenous carbohydrate ligand for ELAM-1. The present invention provides a family of glyco-amino acids or glycopeptides which bind as the endogenous ligands and thereby block other selectin receptors such as LECAM-1 receptors.

The glyco-amino acids or glycopeptides may also be labeled using standard radioactive, fluorescent, enzymic or other label for analytical or diagnostic purposes.

We have discovered that in order for a glyco-amino acid or glycopeptide of the invention to bind to a selectin receptor the glycopeptide need not include the identical atoms in the identical configuration as per glyco-amino acids or glycopeptides of structural formula I, but preferably have (1) a stable three dimensional conformation as shown in structure I or (2) a substantially equivalent configuration to that shown in structural formula I. The equivalency of any other ligand will relate to its physical three dimensional structure and the electron configuration of the molecule and in particular the charge and lipophilicity related characteristics. In order for a glyco-amino acid or glycopeptide of the invention to have a substantially equivalent structure to that shown in structural formula I, the glyco-amino acid or glycopeptide would preferably bind to a selectin receptor when the molecule is allowed to bind to the receptor under physiological conditions.

It has been indicated that "D", "E" or "G" of structural formula I may be a linker which may be attached to any suitable or attachable moiety including a ceramide or a protein or a peptide and is preferably a group with a reactive group thereon which allows it to covalently bind to a substrate or a pharmaceutically active drug. In one embodiment of the invention the "linker" connects one or more ligands to a support base. The support base is then contacted with a sample to assay for the presence of a desired selectin in the sample.

The "linker" can be used to attach a pharmaceutically effective drug to the glyco-amino acid or glycopeptide at the "D", "G" or "E" position, with the proviso that either G is H or M$^2$ is H when E is —(CH$_2$)$_w$—[K—(CH$_2$)$_q$]$_r$—M$^1$ and either E is H or M$^1$ is H when G is —[K—(CH$_2$)$_q$]$_r$—M$^2$. The (Glyco-amino acid or Glycopeptide-Linker-Drug) conjugate thus formed provides an effective drug delivery system for the linked drug.

NSAID or non-steroidal, anti-inflammatory drugs such as naproxen or ibuprofen which act as anti-inflammatory agents could be administered bound to the modified glyco-amino acid or glycopeptide and could be administered systemically in smaller amounts than usual while obtaining an equivalent effect or even greater anti-inflammatory effect at the site of inflammation. Any other drugs which might be attached include, but are not limited to, antibiotics, vasodilators and analgesics. Such a drug delivery system would reduce any systemic effect normally caused by the drug in that the drugs could be administered in amounts of one-half to one-tenth the normal dose and still obtain the same anti-inflammatory result at the site of inflammation.

Assaying Compounds of the Invention

The glyco-amino acids or glycopeptides can be assayed for their ability to bind to a selectin receptor and/or block the binding site of the receptor and thereby prevent a natural ligand from binding to the selectin receptor. Several assays may be used as described below.

ELISA Assay

An ELISA assay (Foxall et al, *The Journal of Cell Biology* (1992) 117:895) is preferably used which consists of the following three steps:

1. 2,3 sLex glycolipid is transferred into microtitre wells as solutions and then evaporated off. Excess, which remained unattached, is washed off with water. The wells are then blocked with a blocking agent, preferably BSA.
2. Preparation of "multivalent" receptor of the Selectin-IgG chimera is carried out by combining the respective chimera with biotin labelled goat F(ab')$_2$ anti-human IgG (Fc specific) and streptavidin-alkaline phosphatase diluted appropriately and incubated. This allows the soluble multivalent receptor complex to form.
3. Potential inhibitors such as glyco-amino acids or glycopeptides of structural formula I are allowed to react with the soluble receptor. This solution is then placed in the microtitre wells that are prepared in step 1. The plate is incubated to allow the soluble receptor to bind to its natural ligand. In the presence of a strong inhibitor only a few of the receptors should be free to bind to the microtitre plate coated with the natural ligand.

The positive control is the signal produced by the soluble receptor when it is allowed to react with the natural ligand in the microtitre wells in the absence of any inhibitor. This is considered 100% binding. The signal produced by the receptor that is previously treated with an inhibitor (recorded as O.D.), is divided by the signal produced by the positive control and multiplied by 100 to calculate the % receptor bound to the well in the presence of the inhibitor. The reciprocal of this is the % inhibition.

Identification of Putative ELAM-1 Ligands Using Recombinantly Produced Receptor A complete cDNA for the ELAM-1 receptor was obtained by PCR starting with total RNA isolated from IL-1 stimulated human umbilical vein endothelium. The resulting cDNA was inserted into the CDM8 plasmid (see Aruffo et al., Proc Natl Acad Sci USA (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua et al., *Science*, (1989) 243:1160; Polte et al., *Nucleic Acids Res* (1990) 18:1083; Hession et al., *Proc Natl Acad Sci USA* (1990) 87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT patent application WO90/13300 which was published Nov. 15, 1990, which is incorporated herein by reference).

COS cells, expressing membrane-bound ELAM-1, are metabolically radiolabeled with $^{32}PO_4$. These labeled cells can be used as probes in two assay systems to screen for recognition of glyco-amino acids or glycopeptides of structural formula I. More specifically, the ligands may be adsorbed to the bottoms of PVC microtiter wells or resolved on TLC plates. In either assay the compounds may be probed for their ability to support adhesion of ELAM-transfected COS cells, untransfected COS cells, or COS cells transfected with a plasmid containing an irrelevant cDNA, under conditions of controlled detachment force (see Swank-Hill et al., *Anal Biochem* (1987) 183:27; and Blackburn et al., *J Biol Chem.* (1986) 261:2873 each of which is incorporated herein by reference to disclose the details of such assaying methodology).

P-selectin/HL-60 Assay

The glyco-amino acids or glycopeptides of structural formula I can be tested for their ability to inhibit P-selectin binding to its native ligand. A generalized procedure for testing the ligands is given below. A P-selectin/HL-60 assay is preferably used which consists of the following steps:

1. HL-60 cells are harvested and pelleted by centrifugation. The cells are washed, counted and the volume adjusted appropriately.
2. PVC microtiter plate is blocked with a blocking agent, and washed with TBS-BSA.
3. P-selectin is diluted appropriately in BSA-TBS Ca containing goat F(ab')$_2$anti-human IgG (Fc spec) and streptavidin-alkaline phosphatase. Positive controls have DMF added to equal the highest concentration of DMF in the sample compounds.
4. Ligands are incubated at room temperature with brisk rotation. The tubes are centrifuged to pellet insoluble material. Supernatant from the centrifugation is applied to quadruplicate wells and cells are added. Plate controls are HL-60 cells alone, HL-60 cells with Ab-AP, P-selectin solution with no cells, and the positive test controls described above. The plate is incubated, the cells are pelleted by centrifugation and washed.

Para-nitrophenylphosphonate is added to the plate. Color is allowed to develop. Aliqouts from each well is transferred to a polystyrene microtiter plate and O.D. read at 405 nm. The positive control is the signal produced by the soluble receptor when it is allowed to react with the natural ligand in the absence of any inhibitor. This is considered 100% binding. The signal produced by the receptor that is previously treated with an inhibitor (recorded as O.D.), is divided by the signal produced by the positive control and multiplied by 100 to calculate the % receptor bound to the well in the presence of the inhibitor. The reciprocal of this is the % inhibition.

Stamper-Woodruff Assay (General)

Lymphocytes are known to circulate from blood to lymphoid tissues via high endothelial venules (HEV) on lymph nodes. L-selectin is expressed on the surface of lymphocytes and is believed to mediate lymphocyte adhesion by binding to the natural ligand on the HEV. The glyco-amino acids or glycopeptides of structural formula I can be tested for their ability to bind to a selectin receptor and/or block the binding site of the receptor and thereby prevent a natural ligand from binding to the selectin receptor. See, for example, Stoolman et al, *The Journal of Cell Biology* (1983) 96:722. The Stamper-Woodruff assay is well known in the an, and generally consists of the following three steps:

1. Preparation of the lymphocytes:

(a) The lymphocytes are obtained from the mesenteric nodes of female Swiss Webster mice, by gently teasing tissues with phosphate buffered saline (PBS). The cells are obtained by gently squeezing the cells from the tissues. The cells are dispersed and the cell clumps are removed. The single cell suspension is suspended, washed, and kept on ice until use (less than two hours). Cells are counted and prepared at an appropriate concentration.

(b) The superficial and deep cervical lymph nodes of female Sprague-Dawley rats are dissected and prepared in the same way as the mice.

2. Preparation of frozen sections:

Superficial or deep cervical lymph nodes are dissected from the animals, snap frozen, and immediately placed in a cryostat for sectioning. 10-μm sections are prepared and transferred onto glass slides, and air dried.

3. Potential inhibitors are added to lymphocyte suspensions 10–30 minutes before the start of the binding assay, and unless otherwise stated, are present throughout the subsequent binding incubation.

The frozen sections are used in the order in which they are cut. Aliquots of untreated lymphocytes (positive control), suspensions containing fucoidin (negative control) and suspensions containing potential inhibitors are layered on the sections in an arbitrary sequence such that the control and each test substance are represented once in a series.

The binding of the lymphocytes to the HEV is easily distinguishable from binding elsewhere by virtue of the characteristic picture of tightly packed, darkly stained lymphocytes overlaying the histologically distinctive HEV. The number of adherent lymphocytes on each HEV are counted and the average number of adherent cells per HEV (cells bound per HEV) is calculated. The results are expressed as a percent of relative binding, wherein the positive control is considered to be 100% binding.

One mechanism by which the glyco-amino acids or glycopeptides of the invention could mediate intercellular events would involve the recognition of these glyco-amino acids or glycopeptides on one cell (e.g., an endothelial cell) by a specific carbohydrate-binding protein (lectin) on an opposing cell (e.g., a leukocyte). Data generated in connection with the present invention indicate that acidic glycolipids isolated from leukocytes and ELAM-1 function as such an oligosaccharide-lectin pair, participating in the interaction of neutrophils with the surface of cells of activated vascular endothelium. Many protein-protein interactions have been implicated in neutrophil-endothelium transmigration (see Lo et al, *J Immunol* (1989) 143:3325; Osborn et al, *Cell* (1989) 59:1203; Larsen et al, *Cell* (1989) 59:305; and Arnaout *Blood* (1990) 75:1037). While not wishing to be bound to any theory, the present inventors believe it is likely that this lectin-carbohydrate interaction is only one step in a series that result in neutrophil extravasation.

The adhesion of selectins to glyco-amino acids or glycopeptides of the invention has been tested. Accordingly, such glyco-amino acids or glycopeptides would be useful in mediating a specific, but possibly weak adhesion that is then stabilized and elaborated by the participation of other receptors. Glyco-amino acids or glycopeptides with the structural and functional characteristics described herein, or modifications of these structures, are capable of blocking the interaction of neutrophils with activated vascular endothelium mediated by ELAM-1, and hence provide useful pharmaceutically active agents which can interrupt the adverse effects involved in the interaction of ELAM-1 and circulating neutrophils, e.g., prevent or reduce inflammation. However, the Applicants do not intend to be limited to the above mechanism of action that may account for the prophylactic or therapeutic effects of the glyco-amino acids or glycopeptides of the current invention.

Method of Synthesis (General)

The glyco-amino acids or glycopeptides of structural formula I can be made using the general synthesis scheme as described below in Scheme I, wherein X is $R_1$, $OR_1$ or $CH_2OR_1$;

Y is $R_2$ or $OR_3$;

$R_1$ is H, an alkyl group containing 1 to 6 carbon atoms, aryl group;

$R_2$ is an alkyl group containing 0 to 3 carbon atoms; said alkyl may be substituted with up to 2 OH groups;

$R_3$ is an O-alkyl group containing 1 or 2 carbon atoms; and said O-alkyl may be substituted with 1 OH groups;

$R_5$, $R_6$ is a protecting group, preferably acetate or benzyl group;

$R_7$, $R_8$ is an alkyl or aryl group.

In general, as indicated in Scheme I, compound (1a) is activated and a protected amino acid (1b), preferably proline, homoproline, leucine, isoleucine, tyrosine, tryptophan or histidine, is reacted with it to yield (1c). The glycopeptide of the general structure (1c) is deprotected, activated and reacted with another protected amino acid (1d), preferably phenylalanine, O-benzyl serine, diphenyl-phenylalanine, methoxy tyrosine, bromo-phenylalanine or phenylglycine, to yield (1e). The glycopeptide of the general structure (1e) is then deprotected to yield (1f), a glycopeptide of the structural formula I.

Alternatively, 1a can react with suitably protected peptides, prepared by conventional peptide syntheses, with free amino terminal to provide 1e.

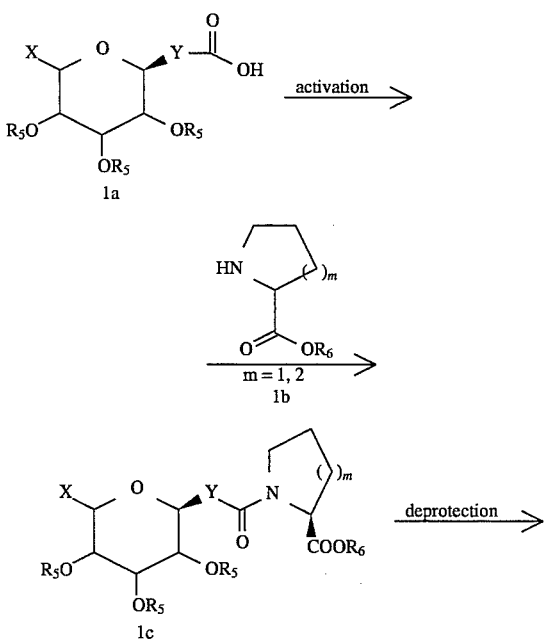

Scheme 1

-continued
Scheme 1

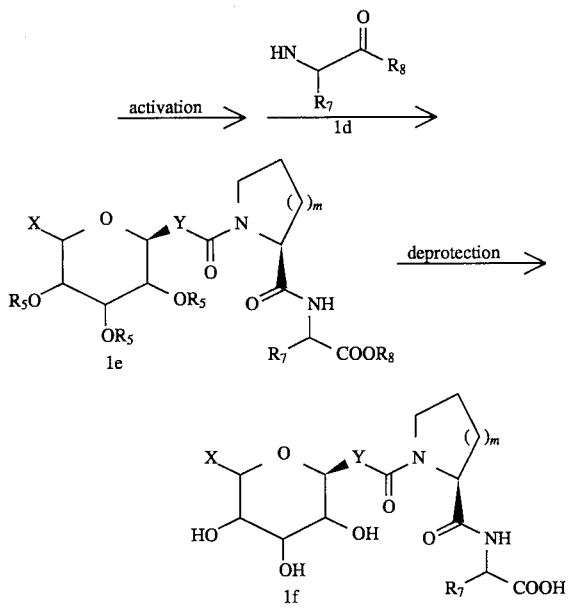

Use and Administration

The glyco-amino acids or glycopeptides of structural formula I can be administered to a subject in need thereof to treat the subject by either prophylactically preventing inflammation or relieving it after it has begun. The glyco-amino acids or glycopeptides are preferably administered with a pharmaceutically acceptable carrier, the nature of the carrier differing with the mode of administration, for example, oral administration, usually using a solid carrier and I.V. administration a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the glyco-amino acids or glycopeptides directly in transdermal formulations with permeation enhancers such as DMSO. Other topical formulations can be administered to treat dermal inflammation.

A sufficient amount of glyco-amino acids or glycopeptides of the current invention should be administered to bind to a substantial portion of selectin receptors expected to cause or actually causing inflammation so that inflammation can either be prevented or ameliorated. Thus, "treating" as used herein shall mean preventing or ameliorating inflammation and/or symptoms associated with inflammation. Typically, the compositions of the current invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

When determining the dose of glyco-amino acids or glycopeptides of the current invention, which block selectin receptors, to be administered, it must be kept in mind that one may not wish to completely block all of the selectin receptors. In order for a normal healing process to proceed, at least some of the white blood cells or neutrophils must be brought into the tissue in the areas where the wound, infection or disease state is occurring. The amount of glyco-amino acids or glycopeptides of the current invention administered as blocking agents must be adjusted carefully based on the particular needs of the patient while taking into consideration a variety of factors such as the type of disease that is being treated.

It is believed that the glyco-amino acids or glycopeptides of the present invention can be used to treat a wide range of diseases, including diseases such as rheumatoid arthritis, multiple sclerosis and cancer. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the ELAM-1 receptors within hours of the cells being damaged. The receptors are extended into the blood vessels where they adhere to the glyco-amino acids or glycopeptides of the current invention on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the glyco-amino acids or glycopeptides of the invention can be formulated in suppositories and, in some cases, aerosol and intranasal compositions. For suppositories, the vehicle composition will include traditional binders and careers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The glyco-amino acids or glycopeptides of the invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The glyco-amino acids or glycopeptides of structural formula I can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g. Remington's Pharmaceutical Sciences, Mack Publishing Company, Easton, Pa., 17th edition, 1985. The composition or formulation to be administered will, in any event, contain a quantity of the glyco-amino acid or glycopeptide of the invention, adequate to achieve the desired state in the subject being treated.

The various glyco-amino acids or glycopeptides of the invention can be used by themselves or in combination with pharmaceutically acceptable excipient materials as described above. However, glyco-amino acids or glycopeptides of the invention can be made as conjugates wherein the glyco-amino acids or glycopeptides are linked in some manner to a label. By forming such conjugates, the glyco-amino acids or glycopeptides of the current invention act as biochemical delivery systems for the label so that a site of inflammation can be detected.

The glyco-amino acids or glycopeptides of the invention could also be used as laboratory probes to test for the presence of a selectin receptor in a sample. Such probes are preferably labeled such as with a radioactive label. There are a number of known labels including radioactive labeled atoms, e.g. radioactive C, O, N, P, or S, fluorescent dyes and enzyme labels which can be attached to the glyco-amino acids or glycopeptides of the invention using known procedures. Labels as well as methods of attaching labels to sugar moieties are disclosed in U.S. Pat. No. 4,849,513 issued Jul. 18, 1989 to Smith et al. which patent is incorporated herein by reference to disclose labels and methods of attaching labels.

The current invention is shown and described herein in what is considered to be the most practical and preferred embodiments. Publications listed herein are incorporated herein by reference to disclose specific procedures on how to make, and/or use the invention. Further, it is recognized that departures may be made therefrom which are within the scope of the invention, and that obvious modifications will occur to one skilled in the art upon reading this disclosure.

EXAMPLES

The following examples are provided so as to provide those of ordinary skill in the art with a complete disclosure and description of how to make compounds and compositions of the invention and are not intended to limit the scope of what the inventors regard as their invention. Unless indicated otherwise, parts are parts by weight, temperature is in degrees C., and pressure is at or near atmospheric.

EXAMPLE 1

N-[(1-deoxy-α-L-fucopyranosyl)acetyl]-L-proline-L-phenyalanine (2f)

Method 1

To a stirred mixture of 1-allyl-1-deoxy-2,3,4-tri-O-acetyl-α-L-fucopyranose (2a, 10.0 g, 31.9 mmole, Luengo et al, *Tetrahedron Lett.* (1992) 33:6911) in a solvent mixture of acetonitrile:carbontetrachloride:water (80 ml:80 ml:120 ml), 28.0 g (131.2 mmole) of sodium periodate was added, followed by ruthenium trichloride hydrate (145 mg) (Carlsen et al, *J. Org. Chem* (1981)46:3936, Green et al). The reaction became exothermic after 10 minutes and was stirred overnight at room temperature. This mixture was diluted with water (300 ml) and extracted with dichloromethane (2×300 ml). The combined organic layer was washed with water (100 ml) and concentrated. The residual oil was dissolved in ethyl acetate (200 ml) and extracted with saturated sodium bicarbonate (30 ml). The organic layer was washed again with water (20 ml) which was combined with the sodium bicarbonate solution extracts. This combined aqueous extract was acidified with 6N hydrochloric acid solution to pH 1 and extracted with dichloromethane (2×200 ml). The combined organic extracts were washed with water (100 ml), followed by saturated sodium chloride solution, dried over sodium sulfate, filtered and concentrated to give 6.9 g (20.8 mmole, 65%)of (1-deoxy-2,3,4-tri-O-acetyl-α-L-fucopyranosyl)acetic acid (2b) which was used without further purification.

A solution of above acid 2b (3.5 g, 10.5 mmole) in dichloromethane (20 ml) was mixed with pentafluorophenol trifluoroacetate (1.8 ml, 10.5 mmole) followed by pyridine (0.85 ml, 10.5 mmole) (Green et al, *Tetrahedron Letters* (1990) 31:5851). This solution was stirred overnight at room temperature, mixed with L-proline benzyl ester hydrochloride (2.3 g, 9.55 mmole) followed by diisopropylethylamine (5.76 ml, 33 mmole). This reaction mixture was stirred overnight at room temperature and diluted with ethyl acetate (300 ml). This was washed with 5% potassium hydrogen sulfate solution (50 ml), followed by saturated sodium bicarbonate solution (50 ml) and saturated sodium chloride solution, dried over sodium sulfate, filtered and concentrated to provide the crude benzyl ester 2c.

The above crude ester was dissolved in ethyl acetate (100 ml), charged with 10% palladium on carbon (1.0 g) and stirred overnight under a hydrogen atmosphere (balloon pressure). This was filtered through celite and the filtrate was extracted with 5% sodium bicarbonate solution (50 ml). The aqueous extract was acidified with 6N hydrochloric acid solution and extracted with ethyl acetate (2×100 ml). The combined organic extract was washed with water (50 ml), followed by saturated sodium chloride solution (50 ml), dried over sodium sulfate, filtered and concentrated to provide N-[(1-deoxy-2,3,4-tri-O-acetyl-α-L-fucopyranosyl)-acetyl]-L-proline 2d (3.5 g, 8.4 mmole, 80.5%).

To a solution of the acid 2d (150 mg, 0.36 mmole) in dichloromethane (1 ml), L-phenylalanine methyl ester hydrochloride (78 mg, 0.36 mmole) was added, followed by benzotriazol-1-yloxytripyrrolidinophosphonium hexafluorophosphate (188 mg, 0.36 mmole) and diisopropylethylamine (0.197 ml, 1.1 mmole) (Coste et al, *Tetrahadron*

*Letters* (1990) 31:205). The mixture was stirred overnight at room temperature and eluted on a silica gel column (50 ml) with ethyl acetate to provide the protected C-glycodipeptide 2e (180 mg, 0.31 mmole, 85%).

A solution of 2e (180 mg, 0.31 mmole) in methanol (2.4 ml) and water (1.2 ml) was added with 2N potassium hydroxide solution (1.2 ml). The solution was stirred overnight at room temperature, acidified and evaporated to dryness. The residue was extracted with 2-propanol (3 ml). Filtration and concentration of the 2-propanol extracted provided 2f (60 mg).

Method 2

A sample of 2b (1.97 g, 6.16 mmol) was dissolved in dichloromethane (25 ml), N-hydroxysuccimide (NHS, 1.0 g, 8.69 mmol) was added to the solution, and the solution was warmed to dissolve the NHS. Dicyclohexylcarbodimide (DCC, 1.41 g, 6.83 mmol) was dissolved in dichloromethane (5 ml) and added to the reaction mixture with stirring. After 5 hours, the reaction mixture was cooled to 4° C., filtered and evaporated. The syrupy residue was taken up in ethyl acetate (50 ml), filtered and washed with water (2×25 ml). The ethyl acetate layer was dried over anhydrous sodium sulfate, filtered and evaporated. After drying under high vacuum 2.5 g (94%) of an amorphous white solid (1-deoxy-2,3,4-tri-O-acetyl-α -L-fucopyranosyl) acetic acid N-hydroxysuccinimide ester (3a) was obtained.

A solution of L-proline-L-phenylalanine (262 mg, 1 mmole) in dimethylformamide (2 ml) was heated with N,O-bistrimethylsilylacetamide (0.057 ml) at 800C. for 10 minutes. This was added to the N-hydroxylsuccinimide ester 3a (430 mg, 1 mmole). This solution was stirred overnight at room temperature and concentrated. The mixture was eluted on a silica gel column (50 ml, chloroform:methanol:water, 300:10:5) to provide protected C-glycodipeptide 3b (500 mg, 0.87 mmole, 87%) which was hydrolysed in a manner similar to the process described for 2e, to yield 2f.

Scheme 2

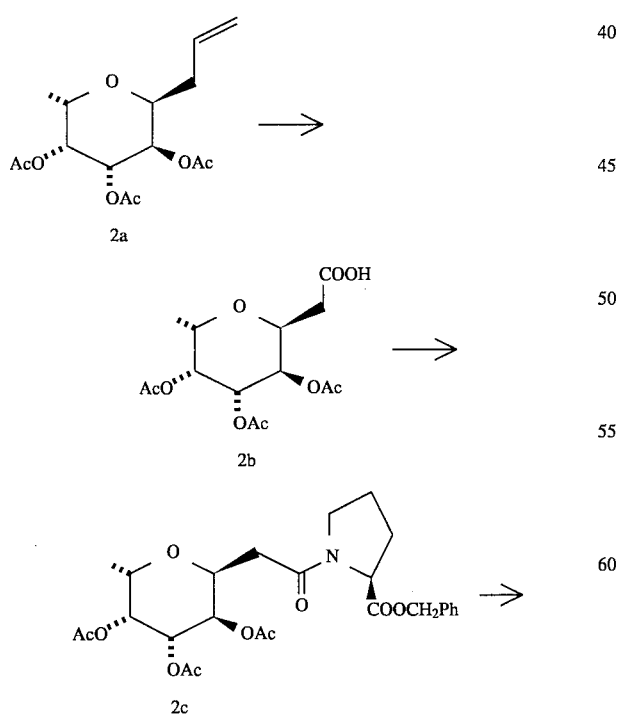

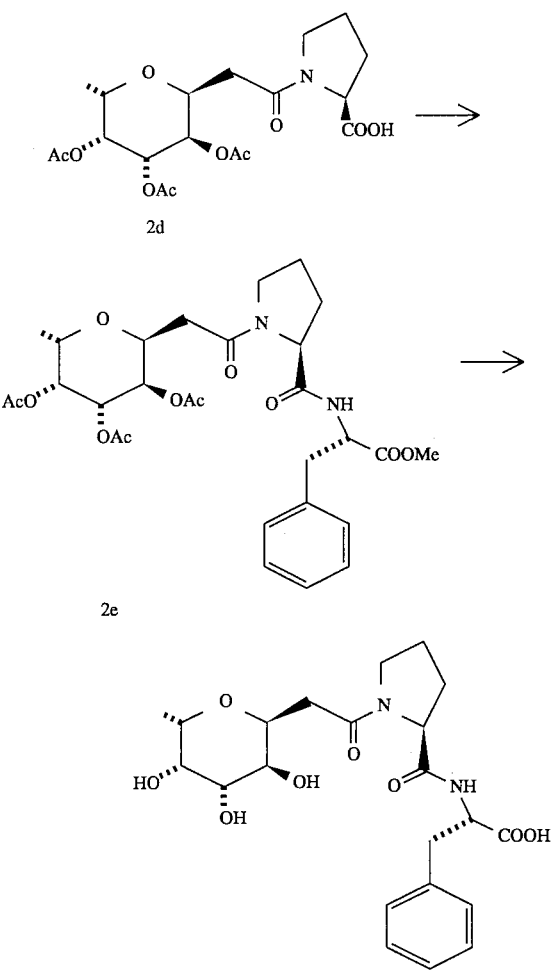

Scheme 3

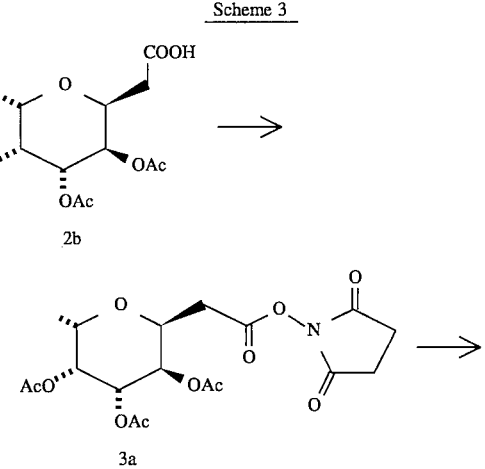

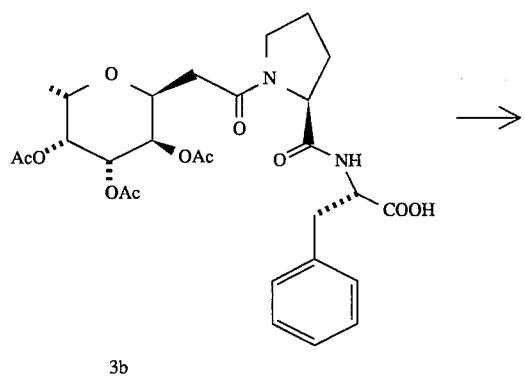

3b

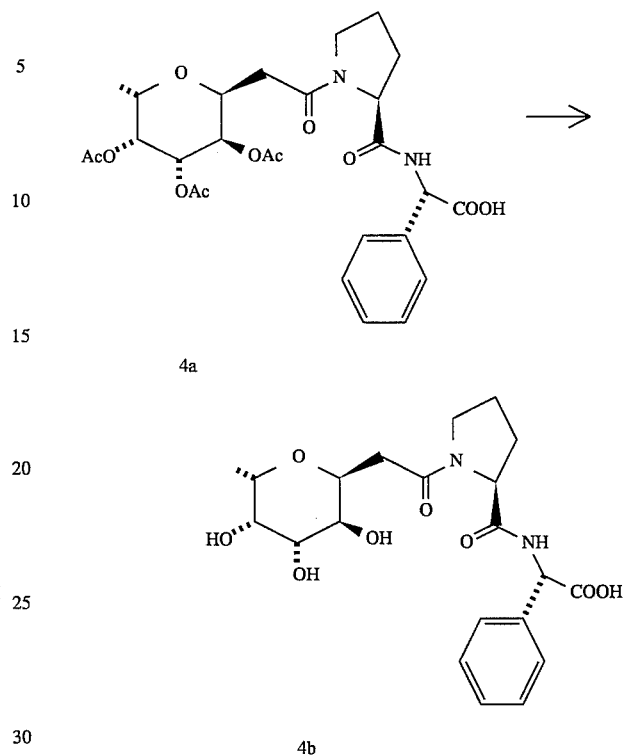

4a

2f

4b

EXAMPLE 2

N-[(1-deoxy-α-L-fucopyranosyl)acetyl]-L-proline-L-phenylglycine (4b)

To a solution of acid 2d (150 mg, 0.36 mmole) in dichloromethane (1 ml), L-phenylglycine methyl ester hydrochloride (78 mg, 0.36 mmole) was added, followed by benzotriazol-1-yloxytripyrrolidinophosphonium hexafluorphosphate (188 mg, 0.36) and diisopropylethylamine (0.197 ml, 1.1 mmole). The mixture was stirred overnight and eluted on a silica gel column (50 ml) with ethyl acetate to provide the protected C-glycodipeptide 4a (180 mg, 0.31 mmole, 85%). A solution of 4a (180 mg, 0.31 mmole) in methanol (2.4 ml) and water (1.2 ml) was mixed with 2N potassium hydroxide solution (1.2 ml). The solution was stirred overnight at room temperature, acidified and evaporated to dryness. The residue was extracted with 2-propanol (3 ml). Filtration and concentration of the 2-propanol extracted provided 4b (60 mg).

Scheme 4

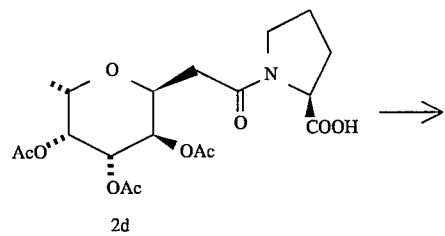

2d

EXAMPLE 3

N-[(1-deoxy-α-L-fucopyranosyl)acetyl]-L-alanine-L-proline-L-phenylalanine(5c)

Method 1

A solution of L-alanine-L-proline-L-phenylalanine (5a, 50 mg, 0.15 mmole) in dimethylformamide (0.5 ml) was stirred with N,O-bistrimethylsilylacetamide (75 μl) at 80° C. for 5 minutes. This was added to activated ester 3a (65 mg, 0.15 mmole) followed by a catalytic amount of 4-N,N'-dimethylaminopyridine. This mixture was stirred overnight at room temperature and concentrated. The residue was worked up with chloroform and diluted hydrochloric acid solution. The crude protected C-glycotripeptide (5b) was hydrolysed similarly as described in Example 1 to provide 5c (40 mg, 0.076 mmole, 51%).

Method 2

A solution of L-alanine-L-proline-L-phenylalanine methyl ester trifluoroacetic acid salt (6a, 2.5 g, 5.4 mmole), prepared from conventional peptide synthesis, and activated ester 3a (3.3 g, 5.4 mmole) in dichloromethane (20 ml) was mixed with diisopropylethylamine (1.0 ml, 5.4 mmole). This mixture was stirred at room temperature for 4 hours and diluted with ethyl acetate (300 ml). This combined mixture was washed with 5% potassium hydrogen sulfate (50 ml), followed by saturated sodium bicarbonate solution (30 ml), saturated sodium chloride, dried over sodium sulfate, filtered and concentrated. The residue was purified on a silica gel column (200 ml, dichloromethane:methanol, 92:8) to provide the protected C-glycopeptide 6b (2.4 g, 3.9 mmole, 73%). This sample was hydrolysed in a manner similar to the process described above in Example 1 to yield 5c.

Scheme 5
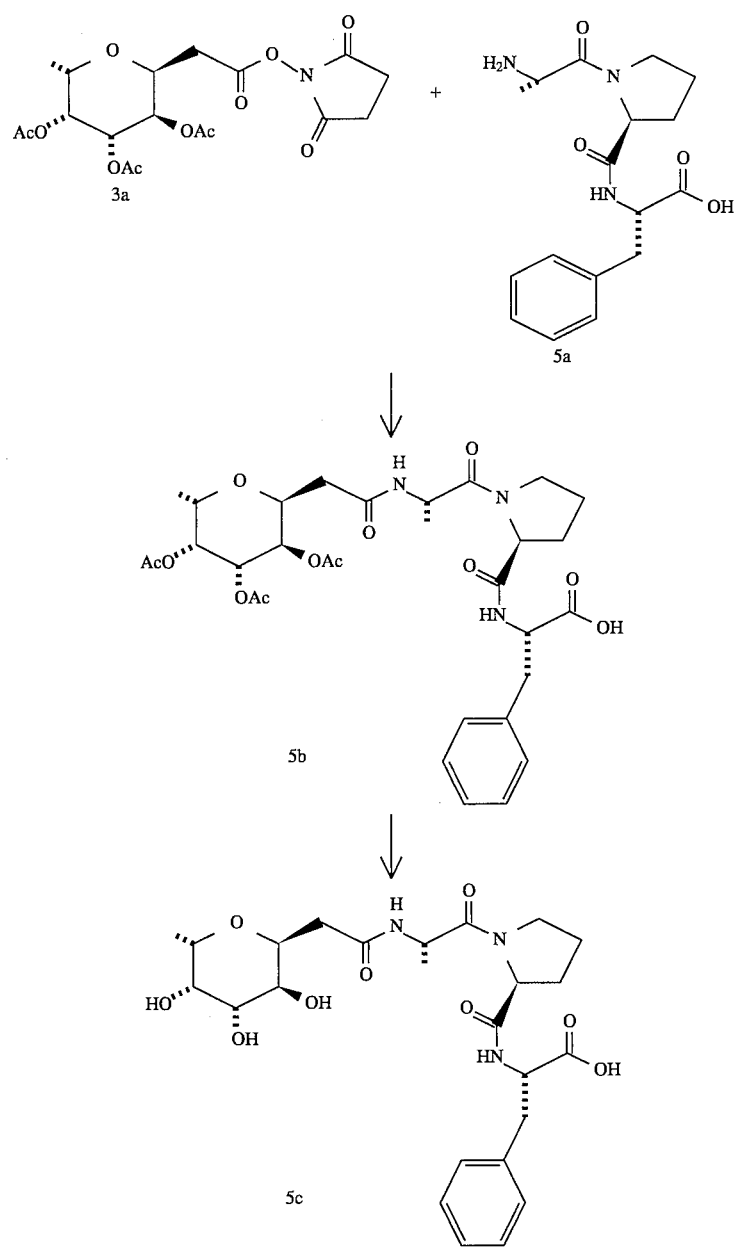

Scheme 6

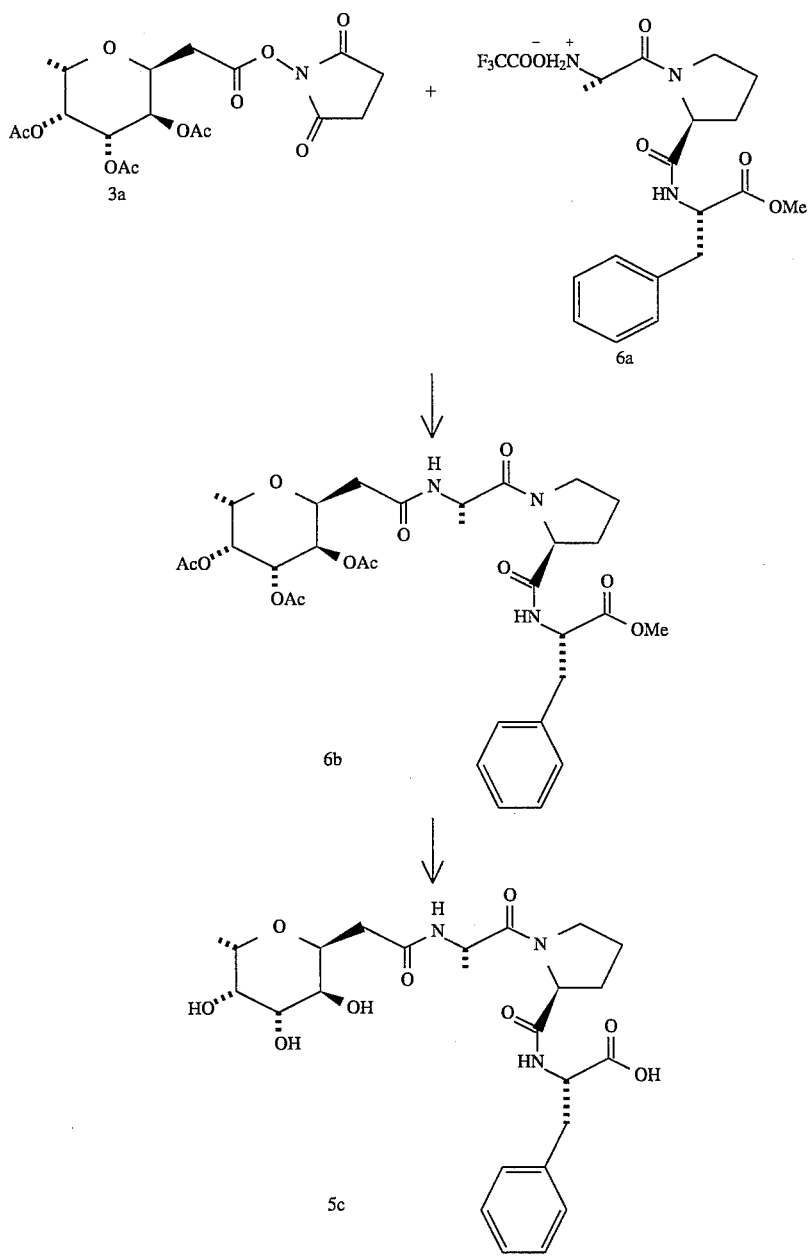

EXAMPLE 4

N-ω-t-butoxylcarbonyl-N α-[(1-deoxy-α-L-fucopyranosyl)acetyl]-L-lysine (7c)

A solution of the activated ester 3a (100 mg, 0.23 mmole) and of N-α-t-butoxycarbonyl-L-lysine (7a, 59 mg, 0.23 mmole) in a 1:1 solvent mixture of water and dimethylformamide (1 ml) was mixed with sodium bicarbonate (100 mg) and stirred overnight at room temperature. The mixture was diluted with ethyl acetate (6 ml) and washed with saturated sodium bicarbonate solution (2 ml). The aqueous layer was separated, washed with another portion of ethyl acetate (2 ml) and acidified with 6N hydrochloric acid solution. This was extracted with dichloromethane (6 ml), the organic layer was washed with saturated sodium chloride solution, dried over sodium sulfate, filtered and concentrated to provide the crude acid 7b (95 mg). The crude acid 7b was hydrolysed in a manner similar to that described in Example 1 to provide 7c (32 mg).

Scheme 7

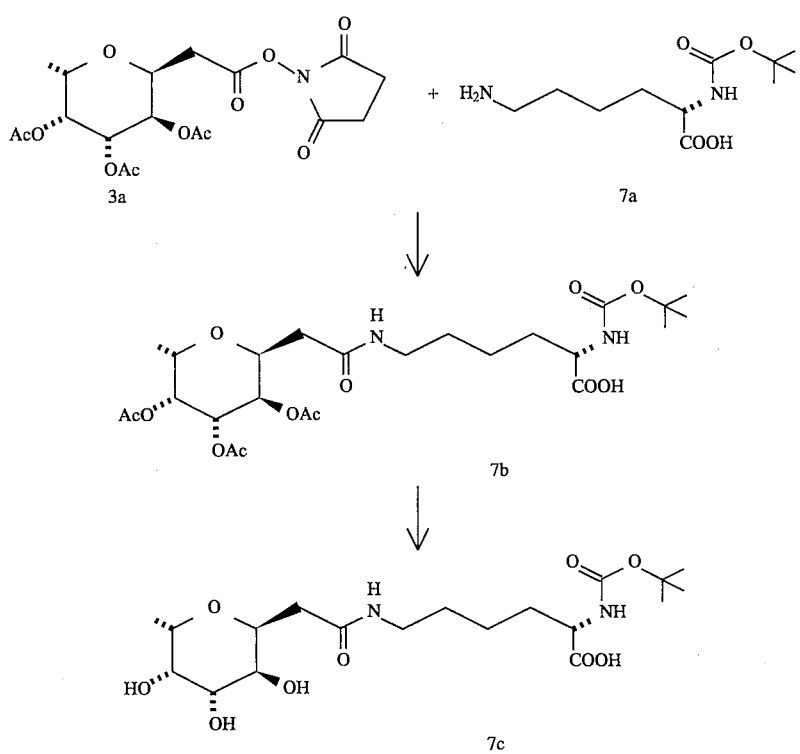

EXAMPLE 5

N-[4-(1-deoxy-α-L-fucopyranosyl)-n-butanoyl]-L-proline-L-phenylalanine (8g)

The aldehyde 8a (2.46 g, 7.78 mmole), obtained by ozone oxidation of 2a, was dissolved in dichloromethane (10 ml) and the ylide t-butyl triphenyl-phosphoranylidene acetate (3.51 g, 9.34 mmole) was added. The reaction was stirred at room temperature for 48 hours and concentrated to dryness. The residue was purified on silica gel column (20% ethyl acetate in hexane) to give the desired product 8b (2.41 g, 75%) as a colorless oil.

The above olefin 8b (2.41 g, 5.83 mmole) was dissolved in methanol (15 ml). A suspension of 10% palladium on carbon (200 mg) in methanol (5 ml) was added to this solution. The reaction was stirred under hydrogen at atmospheric pressure for 28 hrs. The catalyst was removed by filtration through celite. Concentration of the filtrate gave the product 8c (2.38 g, 98%) as a colorless oil.

The above t-butyl ester 8c (177 mg, 0.43 mmole) was dissolved in dichloromethane (5 ml) and trifluoroacetic acid (0.5 ml) was added to it. The reaction was stirred at room temperature for 2 hrs and concentrated to dryness to give the desired product 8d (154 mg, 100%).

A solution of above crude acid 8c (2.2 g, 5.8 mmole) in dichloromethane (10 ml) was added with N-hydroxysuccimide (667 mg, 5.8 mmole) and 1,3-dicyclohexylcarbodimide (5.8 mmole). The mixture was stirred overnight at room temperature and filtered. The solid was rinsed with dichloromethane (5 ml) and the combined filtrates were concentrated to provide the desired activated ester 8e.

A mixture of 8e (387 mg, 0.88 mmole) and L-proline-L-phenylalanine (231 mg, 0.88 mmole) in a 1:1 solvent mixture of dimethylforamide and water (10 ml) was stirred overnight at room temperature with sodium bicarbonate (370 mg). Base and acid extraction with sodium bicarbonate solution, chloroform and diluted hydrochloric acid provided the acid 8f (130 mg).

The above acid 8f was hydrolysed in a manner similar to the process described in Example 1 to provide 8g (60 mg).

EXAMPLE 6

N-[4-(1-deoxy-α-L-fucopyranosyl)-n-butanoyl]-L-phenylalanine (9b)

A solution of ester 8e (166 mg, 0.36 mmole), L-phenylalanine methyl ester hydrochloride (81 mg, 0.36 mmole) and diisopropylethylamine (210 ml, 1.2 mmole) in dichloromethane (2 ml) was stirred overnight at room temperature. The entire mixture was eluted on a silica gel column (50 ml, ethyl acetate:hexane, 3:1) to give the protected ester 9a (160 mg, 85%).

Ester 9a was hydrolysed in a manner similarly to the process described in Example 1 to provide 9b.

EXAMPLE 7

N-[(1-deoxy-α-L-fucopyranosyl)acetyl]-L-proline D-phenylalanine (10b)

To a solution of acid 2d (150 mg, 0.36 mmole) in dichloromethane (1 ml), D-phenylalanine methyl ester hydrochloride (78 mg, 0.36 mmole) was added followed by benzotriazol-1-yloxytripyrrolidinophosphonium hexafluorophsophate (188 mg, 0.36 mmole) and diisopropylethylamine (0.197 ml, 1.1 mmole). The mixture was stirred overnight at room temperature and eluted on a silica gel column (50 ml) with ethyl acetate to provide the protected C-glycodipeptide 10a (170 mg).
The protected dipeptide 10a was hydrolysed in a manner similarly to the process described in Example 1 to provide 10b.
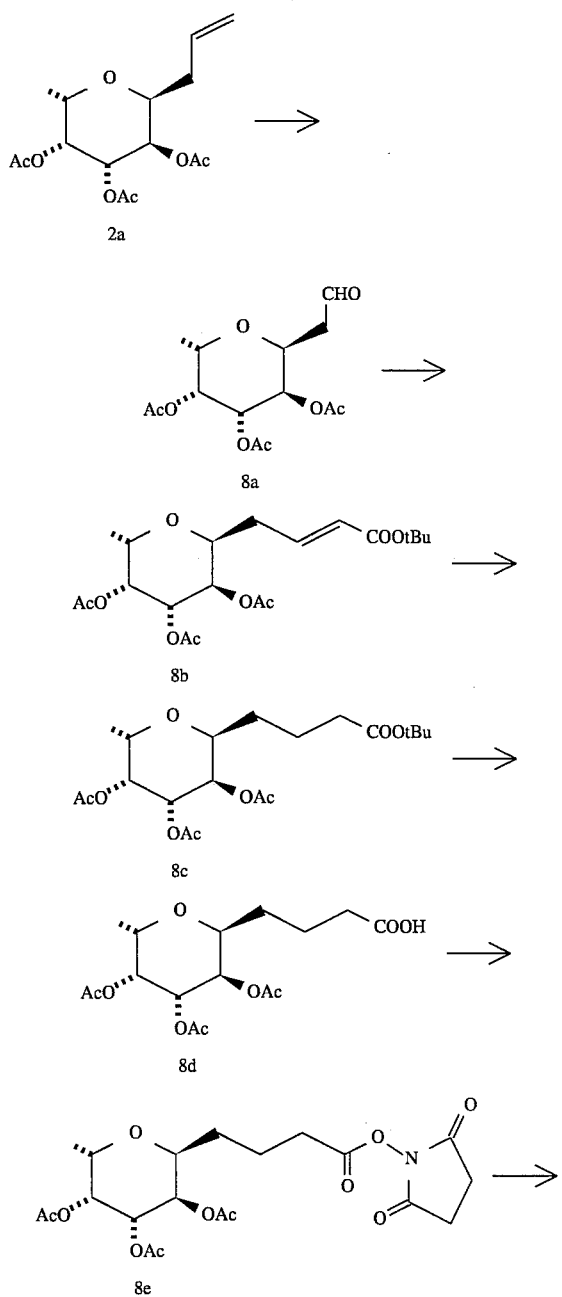
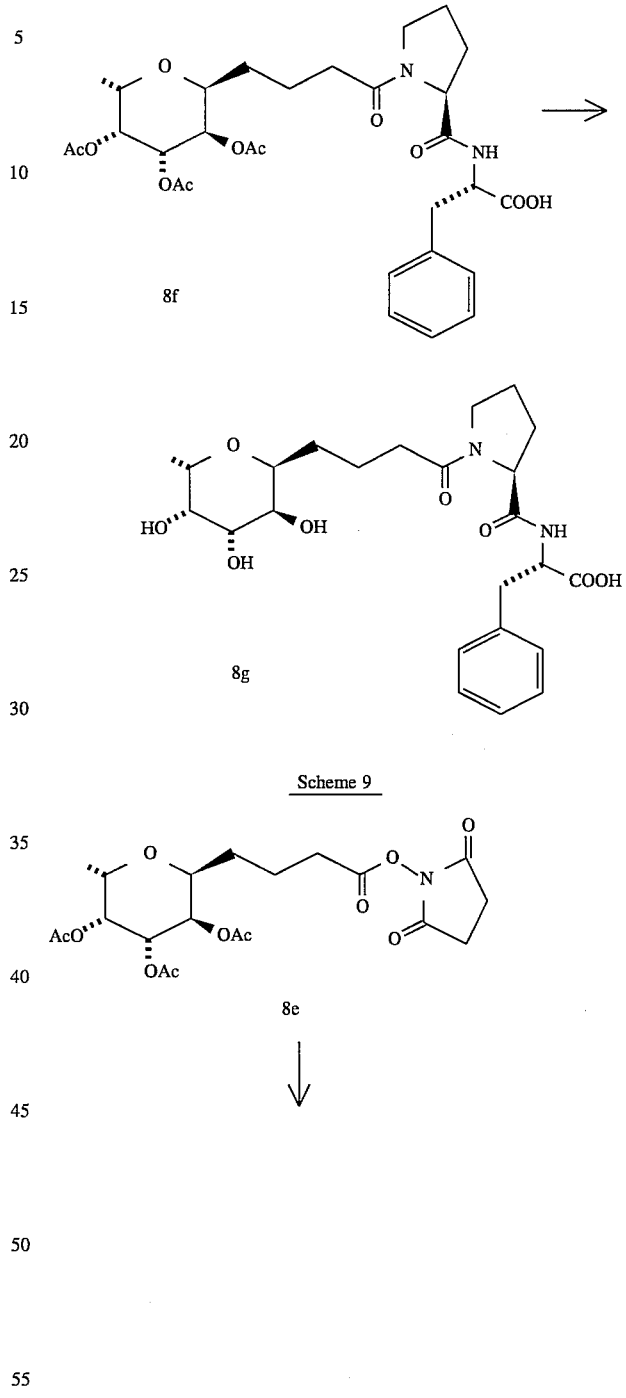

31
-continued
Scheme 9

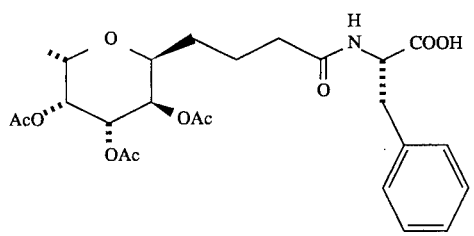

9a

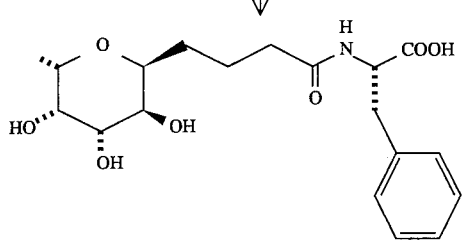

9b

Scheme 10

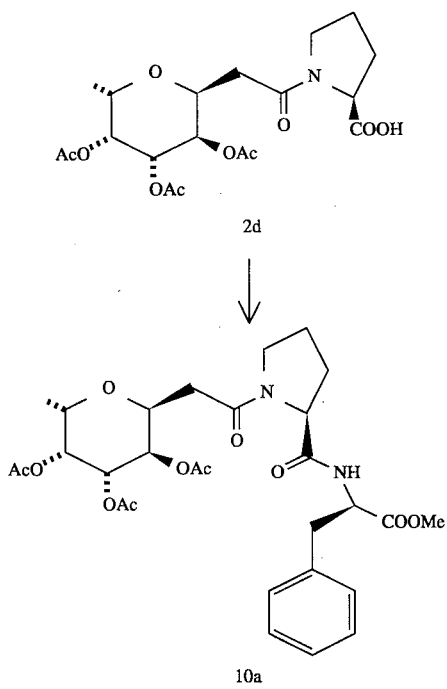

32
-continued
Scheme 10

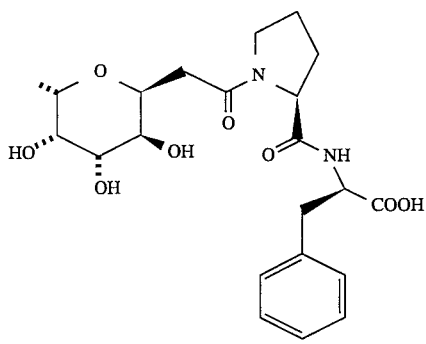

10b

EXAMPLE 8

1-allyl-1-deoxy-2,3,4-tri-O-benzyl-α-L-fucopyranose (11*b*)

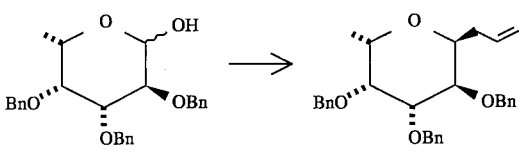

11a      11b

To a solution of 2,3,4-tri-O-benzyl-L-fucopyranose (11*a*, 10.0 g) in acetonitrile (100 ml) at 0° C., allyltrimethylsilane (12 ml) was added followed by trimethylsilyltrifluoromethanesulfonate (14.5 ml). The solution was warmed to room temperature and was stirred for 14 hours at room temperature. The mixture was quenched with water (100 ml) in an ice-water bath. The acetonitrile was evaporated in vacuo and the mixture was extracted with ethyl acetate (3×100 ml). The combined organic extracts were washed with saturated sodium carbonate solution, followed by saturated sodium chloride solution, dried over sodium sulfate, filtered and concentrated. The crude mixture was eluted on a silica gel column (150 ml, hexane:ethyl acetate, 10:1) to provide 1-allyl-1-deoxy-2,3,4 -tri-O-benzyl-α-L-fucopyranose (11*b*, 9.2 g, 79%).

Alternatively, in a two step procedure, 2,3,4-tri-O-benzyl-L-fucopyranose (11*a*, 25 g) was first acetylated with pyridine (25 ml) and acetic anhydride (25 ml) and the crude acetate was dissolved in acetonitrile (150 ml), allyltrimethylsilane (20 ml) and boron trifluoroetherate (16.5 ml) were added to the solution and the reaction mixture was stirred at room temperature for 14 hours. The reaction was worked up and purified as described above. The crude product (11*b*) was pure enough for further reactions.

EXAMPLE 9

(1-deoxy-2,3,4-tri-O-benzyl-α-L-fucopyranosyl)acetic acid (11c)

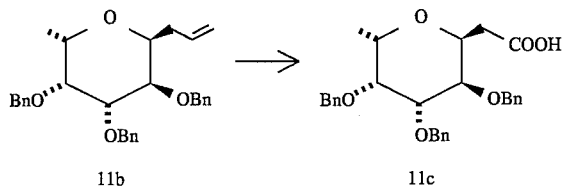

To a stirred mixture of 1-allyl-1-deoxy-2,3,4-tri-O-benzyl-α-L-fucopyranose (11b, 10.0 g, 31.9 mmole) in a solvent mixture of acetonitrile (80 ml), carbontetrachloride (80 ml) and water (120 ml), sodium periodate (40 g, 8 equivalents) was added, followed by ruthenium trichloride hydrate (1.4 g). The reaction became exothermic after 10 minutes and was stirred overnight at room temperature. This mixture was diluted with water (300 ml), extracted with dichloromethane (3×200 ml), and the combined organic layer was washed with water (100 ml) and concentrated. The residual oil was dissolved in ethyl acetate (200 ml) and extracted with saturated sodium bicarbonate (30 ml). The organic layer was washed again with water (20 ml) which was combined with the sodium bicarbonate solution extracts. This combined aqueous extract was acidified with 6N hydrochloric acid solution to pH 1 and extracted with dichloromethane (2×200 ml). The combined organic extracts were washed with water (100 ml), followed by saturated sodium chloride solution, dried over sodium sulfate, filtered and concentrated to give (1-deoxy-2,3,4-tri-O-benzyl-α-L-fucopyranosyl) acetic acid (11c, 4.6 g).

EXAMPLE 10

3(1-deoxy-2,3,4-tri-O-benzyl-α-L-fucopyranosyl)propionic acid (11d)

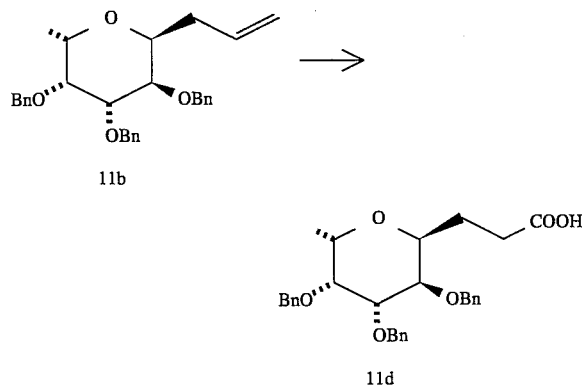

A solution of 9-borabicyclo [3.3.1]nonane (9-BBN, 39.3 ml of 0.5 mM) in tetrahydrofuran was added to 1-allyl-1-deoxy-2,3,4-tri-O-benzyl-α-L-fucopyranose (11b, 12.0 g) at room temperature. The solution was stirred overnight. 1N sodium hydroxide (120 ml) was added very carefully followed by 30% hydrogen peroxide solution (10 ml) and the reaction mixture was stirred for 3 hours at room temperature. The volatile solvents were removed in vacuo, and the resulting solution was extracted with ethyl acetate (3×150 ml). The combined organic extracts were washed with brine, dried over sodium sulfate, filtered and concentrated. The crude mixture was purified on a silica gel column (200 ml, hexane:ethyl acetate, 1:1) to provide 3(1-deoxy-2,3,4-tri-O-benzyl-α-L-fucopyranosyl)-1-propanol (6.8 g).

A solution of the above alcohol (2.5 g) was dissolved in acetone (10 ml), and Jones reagent (6 ml) was added to it at 0° C. The mixture was stirred for 3 hours at room temperature and evaporated. The residue was diluted with water (50 ml) and extracted with ethyl acetate (2×100 ml). The combined organic extracts were washed with brine, dried over sodium sulfate, filtered and concentrated to provide 3(1-deoxy-2,3,4-tri-O-benzyl-α-L-fucopyranosyl) propionic acid (11d, 1.8 g).

EXAMPLE 11

4(1-deoxy-2,3,4-tri-O-acetyl-α-L-fucopyranosyl)but-2-eneoic acid (11f)

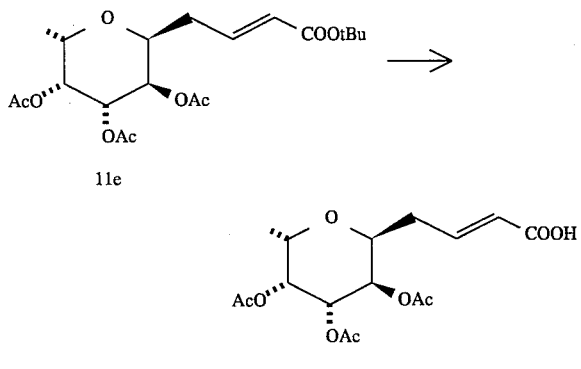

A sample of 11e (3.44 g, 8.31 mmoles) was dissolved in dicholoromethane (10 ml) and trifluoroacetic acid (10 ml) was added to it. The solution was stirred at room temperature for 3 hours and concentrated to dryness. The residue was dissolved in ethyl acetate (100 ml) and washed with saturated sodium bicarbonate solution (5×10 ml). The aqueous layer was acidified with 6N hydrochloric acid to pH 3 and washed with dichloromethane (3×20 ml). The organic extracts were dried over magnesium sulfate, filtered and concentrated to dryness to yield the acid (11f, 100%) as a thick oil which crystallized on standing.

EXAMPLE 12

Sodium (N)-[1-(1-deoxy-α-L-fucopyranosyl)acetyl]-L-Proline-L-phenylalanineol sulfate A sample of 2d (310 mg, 0.72 mmoles) was dissolved in tetrahydrofuran (5 ml) and carbonyl diimidazole (CDI, 1174 mg, 0.72 mmoles) was added. The reaction was stirred at room temperature for 1 hour and phenylalanineol (12a, 109 mg, 0.72 mmoles) was added. The reaction was stirred at room temperature for 48 hours after which the reaction was concentrated to dryness. The residue was dissolved in ethyl acetate (30 ml) and washed with 1N hydrochloric acid (3×10 ml), followed by saturated sodium bicarbonate solution (3×10 ml) and saturated sodium chloride solution (10 ml). The ethyl acetate layer was dried over magnesium surlfate, filtered and concentrated in vacuo. The residue was purified on silica gel (ethyl acetate) to yield (N)-[1-(1-deoxy-α-L-fucopyranosyl)acetyl] -L-proline-L-phenylalanineol (12b, 195 mg, 48%).

A mixture of 12b (0.19 g, 0.34 mmol) and sulfur trioxide-pyridine complex (0.19 g, 1.2 mmol) in pyridine (15 ml) was stirred at 55°–60° C. for 30 minutes. The reaction mixture was cooled, methanol (2 ml) was added and the mixture was stirred for 15 minutes. The reaction mixture was concentrated in vacuo, and purified with silica gel (chloroform-:methanol, 9:1) to yield 12c (230 mg).

12c was dissolved in methanol (20 ml) and a piece of sodium was added to the solution and the mixture was stirred overnight at room temperature. The mixture was deionised with (H+) cation exchange resin and filtered directly onto (Na+) exchange resin and the mixture was stirred for 40 minutes. The reaction mixture was filtered, dissolved in water and lyophilized to yield 12d (0.135 g).

receptor (Foxall et al, *The Journal of Cell Biology* (1992) 117:895). A generalized procedure for testing the ligands is given below.

An ELISA assay is preferably used which consisted of the following three steps:

1. 2,3 sLex glycolipid (25 picomol/well) was transferred into microtitre wells as solutions and evaporated off. Excess, which remained unattached, was washed off with water. The wells were blocked with 5% BSA at room temperature for an hour and washed with PBS containing 1 mM calcium.

2. Preparation of "multivalent" receptor of the Selectin-IgG chimera was carried out by combining the respective chimera (1 μg/mL) with biotin labelled goat $F(ab')_2$

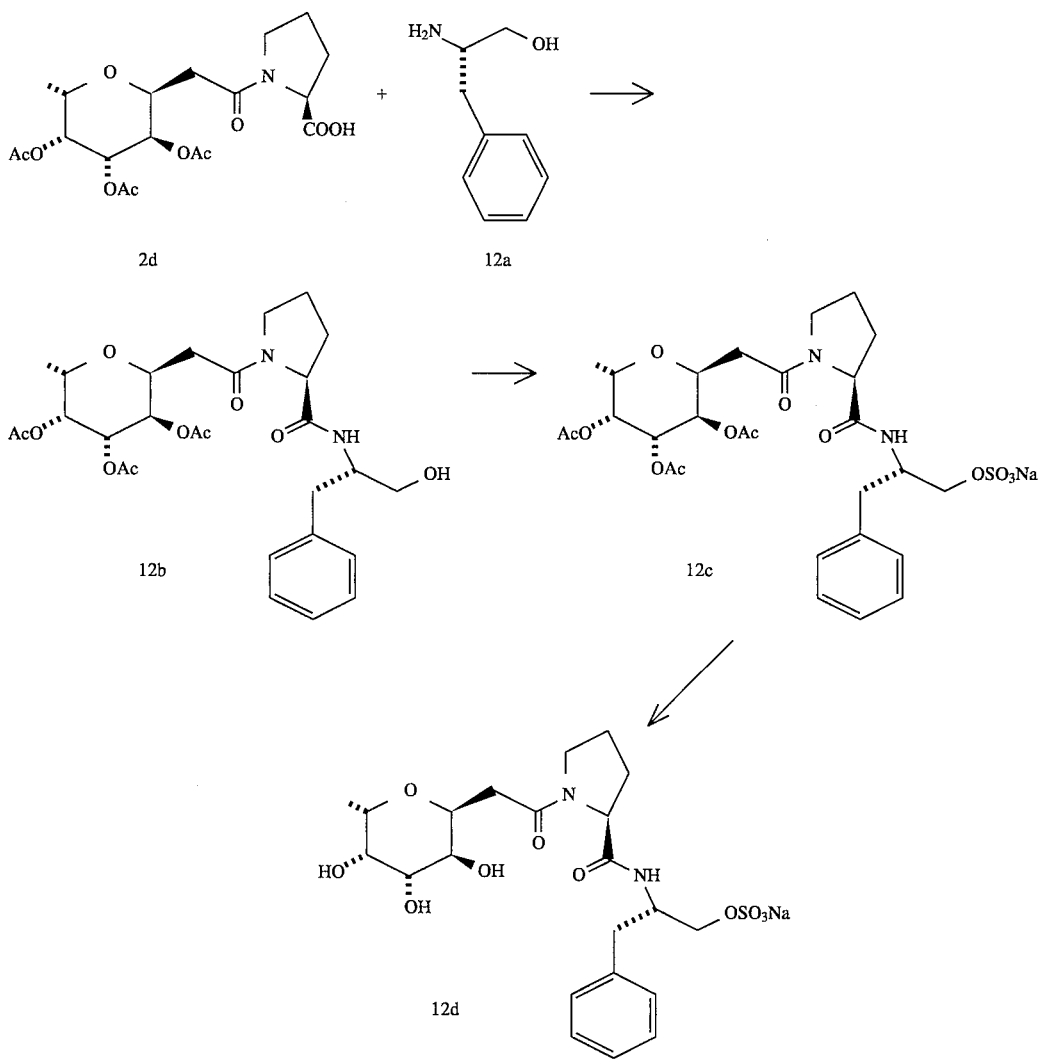

Scheme 12

EXAMPLE 13

Selectin Binding

The glyco-amino acids or glycopeptides of structural formula I can be tested for their ability to bind to a selectin receptor and/or block the binding site of the receptor and thereby prevent a natural ligand from binding to the selectin anti-human IgG (Fc specific) and streptavidin-alkaline phosphatase diluted 1:1000 in 1% BSA-PBS (1 mM calcium) and incubating at 37° C. for 15 min. This allowed the soluble multivalent receptor complex to form.

3. Potential inhibitors such as glyco-amino acids or glycopeptides of structural formula I were allowed to react with the soluble receptor at 37° C. for 45 min. This test assumes that optimal binding, between the soluble phase receptor complex and the inhibitor (non-natural ligand), would occur within this time frame. This solution was placed in the microtitre wells that were prepared in step 1. The plate was incubated at 37° C. for 45 minutes to allow the soluble receptor to bind to its natural ligand. In the presence of a strong inhibitor only a few receptors would be free to bind to the microtitre plate coated with the natural ligand.

Figure 4:
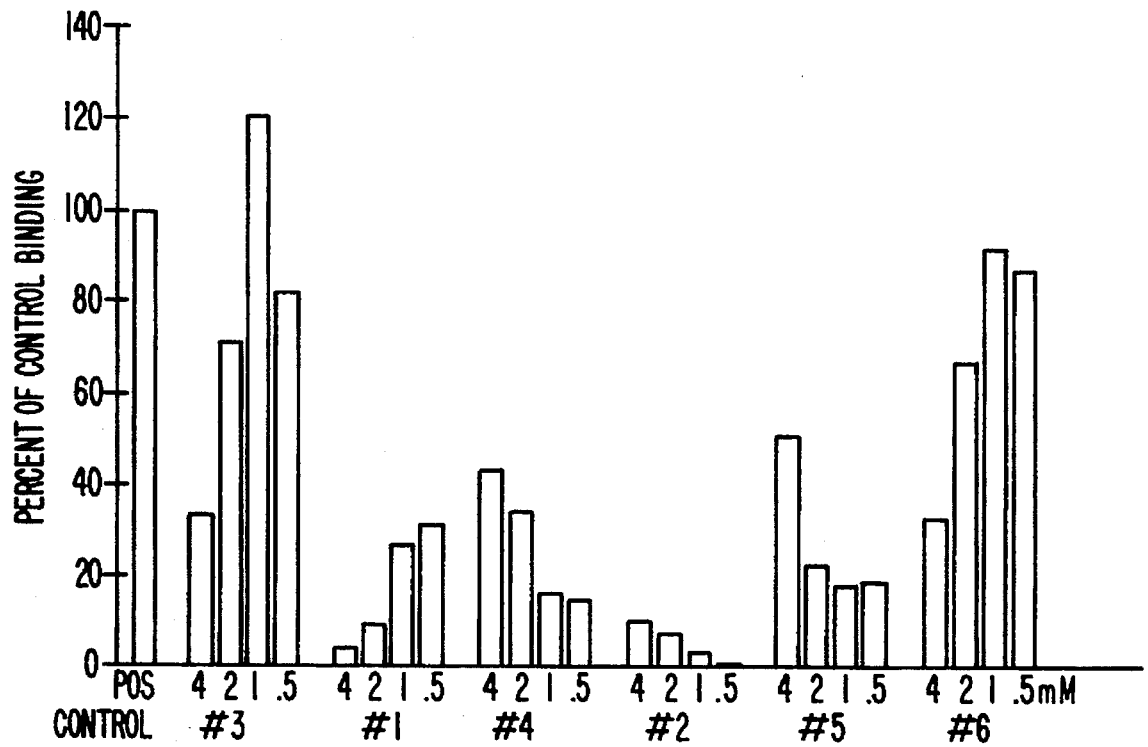
FIG. 4 is a graph that shows that N-[(1-deoxy-α-L-fucopyranosyl)acetyl]-L-proline-L-phenylalanine (#1), N-[(1-deoxy-α-L-fucopyranosyl)acetyl]-L-alanine-L-proline-L-phenylalanine (#2), N-ω-t-butoxylcarbonyl-N-α-[(1-deoxy-α-L-fucopyranosyl)acetyl]-L-lysine (#3), N-[4-(1-deoxy-α-L-fucopyranosyl)n-butanoyl]-L-proline-L-phenylalanine (#4), N-[(1-deoxy-α-L-fucopyranosyl)acetyl]-L-proline-L-phenylglycine (#5), and N-[4-(1-deoxy-α-L-fucopyranosyl)n-butanoyl]-L-phenylalanine (#6) inhibit the binding of sLe$^x$ to L-selectin. The compounds were tested at several concentrations, and the results are expressed as percent of control binding.
Figure 5:
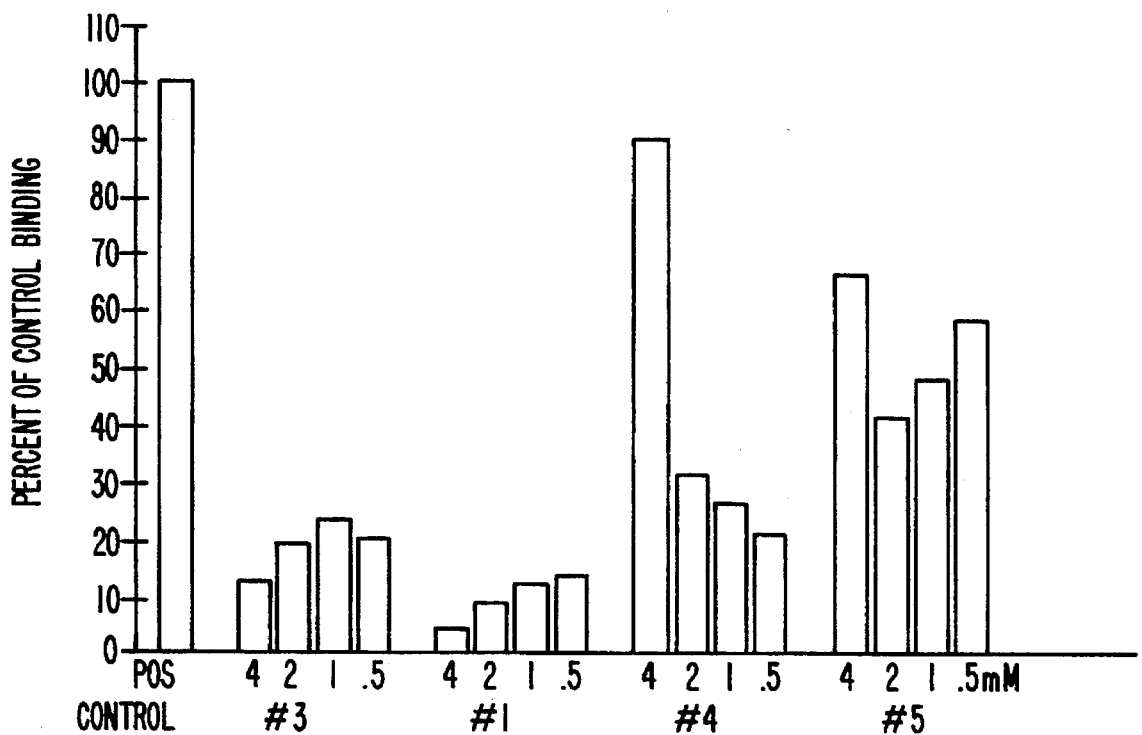
FIG. 5 is a graph that show that N-[(1-deoxy-α-L-fucopyranosyl)acetyl]-L-proline-L-phenylalanine (#1), N,N-ω-t-butoxylcarbonyl-N-α-[(1-deoxy-α-L-fucopyranosyl)acetyl]-L-lysine (#3), N-[4-(1-deoxy-α-L-fucopyranosyl)n-butanoyl]-L-proline-L-phenylalanine (#4), and N-[(1-deoxy-α-L-fucopyranosyl)acetyl]-L-proline-L-phenylglycine (#5) inhibit the binding of sLe$^x$ to P-selectin. The compounds were tested at several concentrations, and the results are expressed as percent of control binding.

The positive control was the signal produced by the soluble receptor when it was allowed to react with the natural ligand in the microtitre wells in the absence of any inhibitor. This was considered 100% binding. The signal produced by the receptor that was previously treated with an inhibitor (recorded as O.D.), was divided by the signal produced by the positive control and multiplied by 100 to calculate the % receptor bound to the well in the presence of the inhibitor. The reciprocal of this is the % inhibition. The results shown in FIGS. 4 and 5 indicate that compounds inhibited L- and P-selectin in their ability to bind to their putative natural ligand.

EXAMPLE 14

P-selectin/HL-60 Assay

The glyco-amino acids or glycopeptides of structural formula I can be tested for their ability to inhibit P-selectin binding to its native ligand. A generalized procedure for testing the ligands is given below. A P-selectin/HL-60 assay is preferably used which consists of the following steps:

1. HL-60 cells were harvested and pelleted by centrifugation. The cells were washed three times with TBS without Ca, counted and the volume adjusted to $1.9 \times 10^6$/ml in 1% BSA-TBS Ca just prior to use.
2. PVC microtiter plate was blocked with 5% BSA-TBS Ca (1 mM) for 1 hour at room temperature. The plate was washed with TBS Ca.
3. P-selectin was diluted to 200 ng/ml in 1% BSA-TBS Ca containing 1:1000 dilutions of goat F(ab')$_2$anti-human IgG (Fc spec) and streptavidin-alkaline phosphatase. Positive controls had DMF added to equal the highest concentration of DMF in the sample compounds.
4. Glyco-amino acids or glycopeptides of structure I were incubated at room temperature for an hour on a rotator, with brisk rotation. The tubes were centrifuged to pellet insoluble material. Supernatant from the centrifugation was applied to quadruplicate wells at 50 µl/well, cells were added at 50 µl/well. Plate controls were HL-60 cells alone, HL-60 cells with Ab-AP, P-selectin solution with no cells and the positive test controls described above. The plate was incubated at 4° C. for 1 hour. Cells were pelleted by centrifugation, washed three times in TBS.

Para-nitrophenylphosphonate was added to 1M diethanolamine buffer, pH 9.8, at 1 mg/ml and 75 µl/well was added to the plate. Color was allowed to develop for about 45 minutes. 50 µl from each well was transferred to a polystyrene microtiter plate and O.D. read at 405 nm.

Figure 6A:
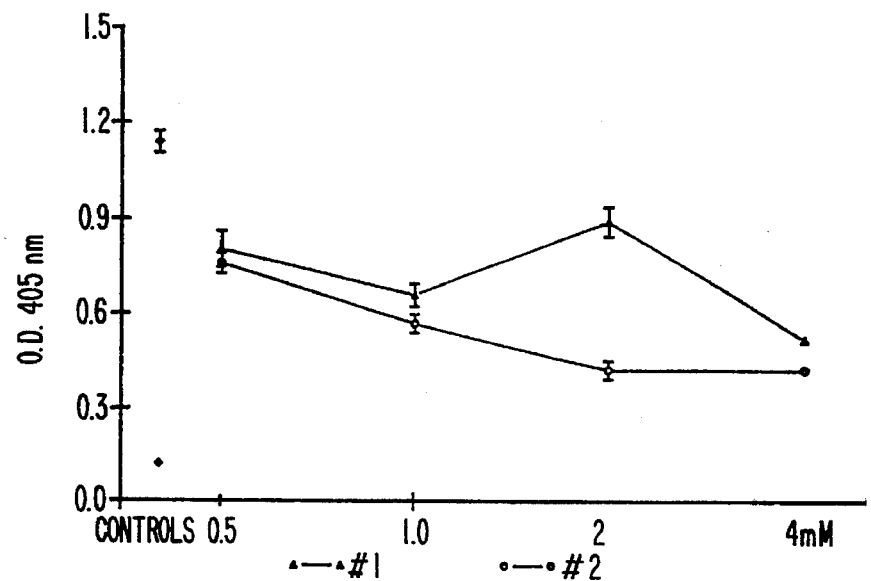
FIG. 6 has graphs showing the ability of N-[(1-deoxy-α-L-fucopyranosyl) acetyl]-L-proline-L-phenylalanine (#1), and N-[(1-deoxy-α-L-fucopyranosyl)acetyl]-L-alanine-L-proline-L-phenylalanine (#2) to inhibit the binding of sLe$^x$ to P-selectin in the HL-60 assay. The compounds were tested at several concentrations.
Figure 6B:
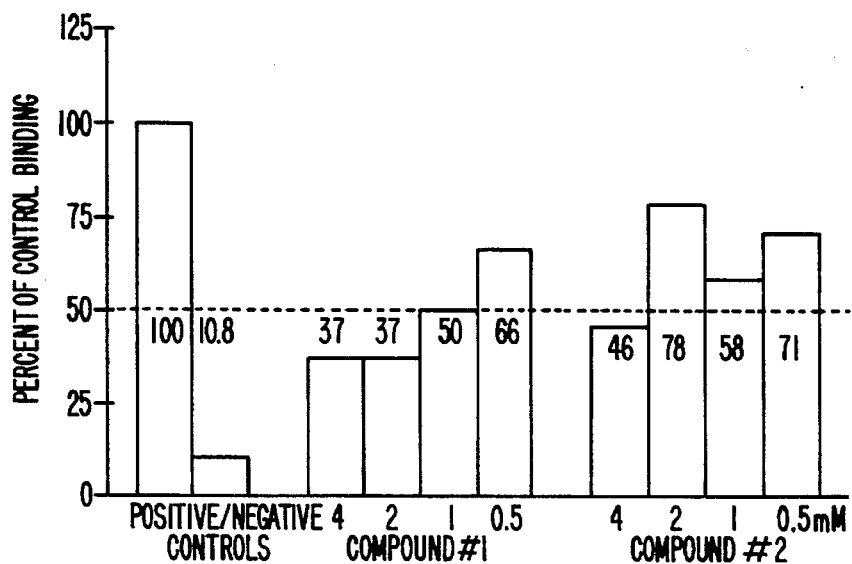

FIG. 6 has graphs showing the ability of N-[(1-deoxy-α-L-fucopyranosyl) acetyl]-L-proline-L-phenylalanine (#1), and N-[(1-deoxy-α-L-fucopyranosyl) acetyl]-L -alanine-L-proline-L-phenylalanine (#2) to inhibit the binding of sLe$^x$ to P-selectin. The compounds were tested at several concentrations.

EXAMPLE 15

Stamper-Woodruff Assay

Lymphocytes are known to circulate from blood to lymphoid tissues via high endothelial venules (HEV) on lymph nodes. L-selectin is expressed on the surface of lymphocytes and is believed to mediate lymphocyte adhesion by binding to the natural ligand on the HEV. The glyco-amino acids or glycopeptides of structural formula I were tested for their ability to bind to a selectin receptor and/or block the binding site of the receptor and thereby prevent a natural ligand from binding to the selectin receptor. See, for example, Stoolman et al, *The Journal of Cell Biology* (1983) 96:722. The Stamper-Woodruff assay is well known in the art, and generally consists of the following three steps:

1. Preparation of the lymphocytes:
   (a) The lymphocytes were obtained from the mesenteric nodes of female Swiss Webster mice (23–27 g), by gently teasing tissues by phosphate buffered saline (PBS). Two or three mesenteric lymph nodes from more than two different animals were used. The nodes were put on the well of 6 well plates and 1 ml of PBS was added. The cells were obtained by gently squeezing the cells from the tissues. The cells were dispersed and the cell clumps were removed. The single cell suspension was suspended in Hanks balanced solution (BSS) with 0.5% BSA, washed (2 ml×3), and kept on ice until use (less than two hours). Cells were counted and prepared at $3-4 \times 10^7$ cells/ml.
   (b) The superficial and deep cervical lymph nodes of female Sprague-Dawley rats (180–200 g) were dissected and prepared in the same way as the mice. Four big lymph nodes (two from each rat) were used for lymphocyte preparation.
2. Preparation of frozen sections:
   Superficial or deep cervical lymph nodes were dissected from the animals, snap frozen at −70° C. (dry ice-acetone), and immediately placed in a cryostat for sectioning (IEC Cryostat at −20° C.). 10-µm sections were prepared and transferred onto glass slides. The sections are air dried for 1–2 hours.
3. Potential inhibitors were added to lymphocyte suspensions ($1-2 \times 10^7$ cells/ml at 4° C.) 10–30 min before the start of the binding assay, and unless otherwise stated, were present throughout the subsequent binding incubation. The binding incubations were conducted on glass slides in 1.4 or 2 cm diameter wax circles.

The frozen sections were used in the order in which they are cut. Aliquots of untreated lymphocytes (positive control), suspensions containing fucoidin (100 µg/ml, negative control) and suspensions containing potential inhibitors were layered on the sections in an arbitrary sequence such that the control and each test substance were represented once in a series. The series was repeated until a desired number of replicates had been generated.

The assay was initiated by layering the 4° C. cell suspension onto the sections (at room temperature). The slides were placed on a metal tray, supported on packed ice, and agitated on a gyratory shaker at 60–100 rpm. The temperature of the slides was equilibrated at 7°–10° C. After a 30 minute incubation, the cell suspensions were decanted and the sections were fixed in 3% glutaraldehyde (20 minutes at 4° C.). The slides were placed in racks, washed in Dulbecco's phosphate buffered saline (five, one-second immersions), stained with 0.5% toluidine-blue in a 20% ethanol solution (one, 15–60 second immersion), washed in 95% ethanol (one, two-second immersion), and mounted in glycerol.

The slides were mounted in emersion-oil and the cell adhesion was observed under phase contrast microscope briefly at ×100. The adherent cells were counted on each HEV at ×400. The binding of the lymphocytes to the HEV was easily distinguishable from binding elsewhere by virtue of the characteristic picture of tightly packed, darkly stained lymphocytes overlaying the histologically distinctive HEV. The number of adherent lymphocytes on each HEV were counted on each HEV and the average number of adherent cells per HEV (cells bound per HEV) was calculated. The results were expressed as percent of relative binding, wherein the positive control is considered as 100% binding.

Figure 7:
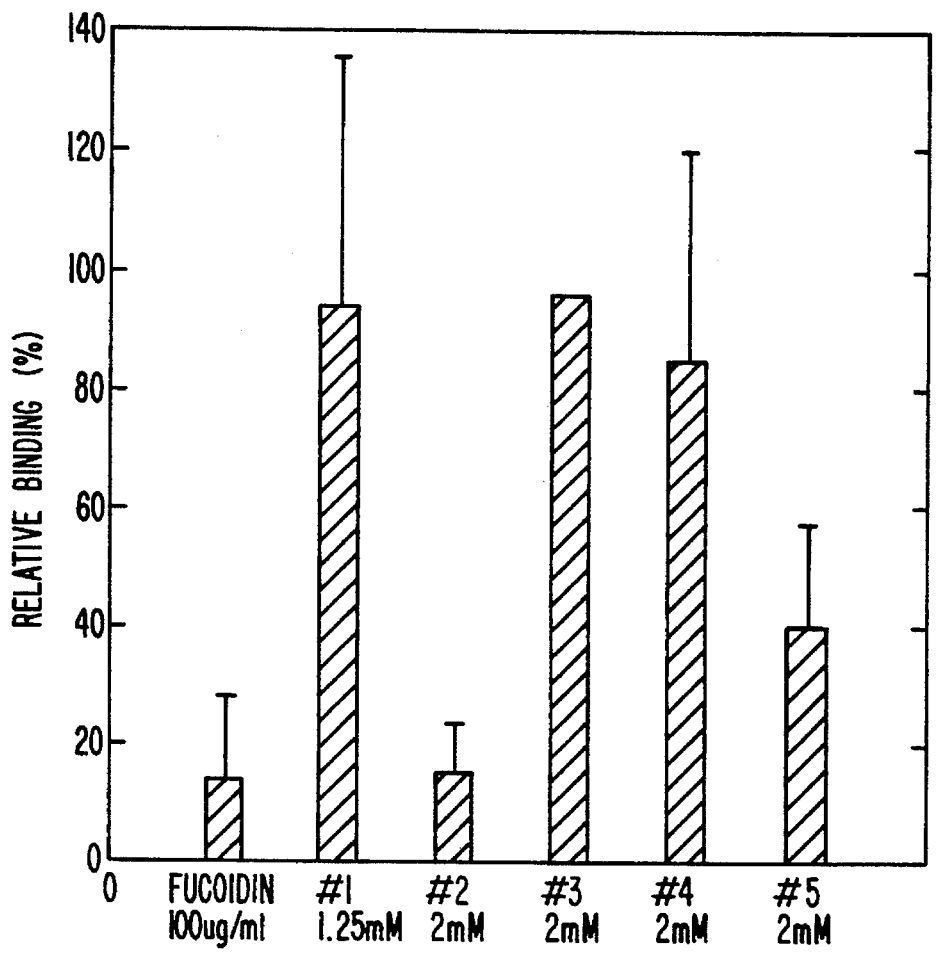
FIG. 7 is a graph showing the inhibitory effects of N-[(1-deoxy-α-L-fucopyranosyl)acetyl]-L-proline-L-phenylalanine (#1), N-[(1-deoxy-α-L-fucopyranosyl) acetyl]-L-alanine-L-proline-L-phenylalanine (#2), N-ω-t-butoxylcarbonyl-N-α-[(1-deoxy-α-L-fucopyranosyl)acetyl] -L-lysine (#3), N-[4-(1-deoxy-α-L-fucopyranosyl) n-butanoyl]-L-proline-L-phenylalanine (#4), and N-[(1-deoxy-α-L-fucopyranosyl)acetyl]-L-proline-L-phenylglycine (#5) in the Stamper-Woodruff assay.

The results shown in FIG. 7 indicate the effect of synthetic glycopeptides {N-[(1-deoxy-α-L-fucopyranosyl)acetyl] -L-proline-L-phenylalanine (#1), N-[(1-deoxy-α-L-fucopyranosyl)acetyl]-L-alanine-L-proline-L-phenylalanine (#2), N-ω-t-butoxylcarbonyl-N-α-[(1-deoxy-α-L-fucopyranosyl)acetyl]-L-lysine (#3), N-[4-(1-deoxy-α-L-fucopyranosyl)n-butanoyl]-L-proline-L-phenylalanine (#4), N-[(1-deoxy-α-L-fucopyranosyl)acetyl]-L-proline-L-phenylglycine (#5) and fucoidin} on cell adhesion.

What is claimed is:

1. A compound comprising the following structural Formula I:

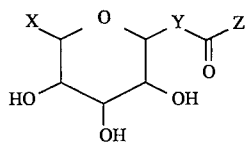

wherein m and u are integers of from 1 to 2; p, q and w are integers of from 1 to 6; r and s are integers of from 0 to 1; and t is an integer of from 0 to 3;

and

A is —COOH or —CH$_2$OSO$_3$H;

B is —R$^1$, —CH(R$^1$)$_2$, —CH$_2$OCH$_2$R$^1$ or —CH$_2$SCH$_2$R$^1$;

D is —L$^1$—(CH$_2$)$_w$—CO—Q or —L$^2$—(CH$_2$)$_w$—CO—Q;

E is H or —(CH$_2$)$_w$—{K—(CH$_2$)$_q$}$_r$—CO—Q with the proviso that when G is H, then E is —(CH$_2$)$_w$—{K—(CH$_2$)$_q$}$_r$—CO—Q;

G is H or —{K—(CH$_2$)$_q$}$_r$—CO—Q with the proviso that when E is H, then G is —{K—(CH$_2$)$_q$}$_r$—CO—Q;

J is —SO$_2$— when D is —L$^1$—(CH$_2$)$_w$—CO—Q; or

J is —CO— or —CS— when D is —L$^2$—(CH$_2$)$_w$—CO—Q;

K is —O—, —S—, —NH—, —S—S—, —CO— or —CONH—;

L$^1$ is —NH—, —CH$_2$—, —NHR$^1$ or —R$^4$;

L$^2$ is —O—, —S—, —NH—, —CH$_2$—, —OR$^4$, —SR$^4$, —NHR$^1$ or —R$^4$;

Q is selected from the group consisting of proteins and peptides;

X is —R$^2$, —OR$^2$ or —CH$_2$OR$^2$;

Y is —(CHR$^3$)$_t$— with the proviso that there are no more than two OH groups; or —O—(CHR$^3$)$_u$— with the proviso that there is no more than one OH group;

wherein

R$^1$ and R$^2$ are independently H, an alkyl group containing 1 to 6 carbon atoms, aryl group or an arylalkyl group;

R$^3$ is H or OH;

R$^4$ is an alkyl group containing 1 to 6 carbon atoms, aryl group or an arylalkyl group; and Z is (a): 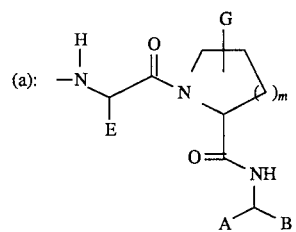

(b): 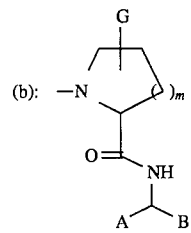

or (c): 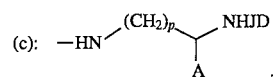

2. The compound of structural formula I of claim 1 wherein Z is

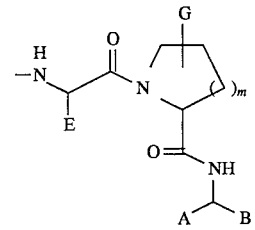

m and u are integers of from 1 to 2; q and w are integers of from 1 to 6; r and s are integers or from 0 to 1; and t is an integer of from 0 to 3;

A is —COOH or —CH$_2$OSO$_3$H;

B is —R$^1$, —CH(R$^1$)$_2$, —CH$_2$OCH$_2$R$^1$ or —CH$_2$SCH$_2$R$^1$;

E is H or —(CH$_2$)$_w$—{K—(CH$_2$)$_q$}$_r$—CO—Q with the proviso that when G is H, then E is —(CH$_2$)$_w$—{K—(CH$_2$)$_q$}$_r$—CO—O;

G is H or —{K—(CH$_2$)$_q$}$_r$—CO—Q with the proviso that when E is H, then G is —{K—(CH$_2$)$_q$}$_r$—CO—O;

K is —O—, —S—, —NH—, —S—S—, —CO— or —CONH—;

Q is selected from the group consisting of proteins and peptides;

X is —R$^2$, —OR$^2$ or —CH$_2$OR$^2$;

Y is —(CHR$^3$)$_t$— with the proviso that there are no more than two OH groups; or —O—(CHR$^3$)$_u$— with the proviso that there is no more than one OH group;

wherein

R$^1$ and R$^2$ are independently H, an alkyl group containing 1 to 6 carbon atoms, aryl group or an arylalkyl group; and R$^3$ is H or OH.

3. The compound of structural formula I of claim 1 wherein Z is

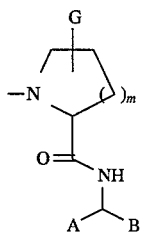

m and u are integers of from 1 to 2; q and w are integers of from 1 to 6; r is an integer of from 0 to 1; and t is an integer of from 0 to 3;

A is —COOH or —CH$_2$OSO$_3$H;
B is —R$^1$, —CH(R$^1$)$_2$, —CH$_2$OCH$_2$R$^1$ or —CH$_2$SCH$_2$R$^1$;
G is —{K—(CH$_2$)$_q$}$_r$—CO—Q;
K is —O—, —S—, —NH—, —S—S—, —CO— or —CONH—;
Q is selected from the group consisting of proteins and peptides;
X is —R$^2$, —OR$^2$ or —CH$_2$OR$^2$;
Y is —(CHR$^3$)$_t$— with the proviso that there are no more than two OH groups; or —O—(CHR$^3$)$_u$— with the proviso that there is no more than one OH group;
wherein
R$^1$ and R$^2$ are independently H, an alkyl group containing 1 to 6 carbon atoms, aryl group or an arylalkyl group; and
R$^3$ is H or OH.

4. The compound of structural formula I of claim 1 wherein Z is

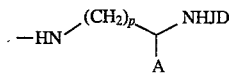

u is an integer of from 1 or 2; p and w are integers of from 1 to 6; and t is an integer of from 0 to 3;

A is —COOH or —CH$_2$OSO$_3$H;
D is —L$^1$—(CH$_2$)$_w$—CO—Q or —L$^2$—(CH$_2$)$_w$—CO—Q;
J is —SO$_2$— when D is —L$^1$—(CH$_2$)$_w$—CO—Q; or
J is —CO— or —CS— when D is —L$^2$—(CH$_2$)$_w$—CO—Q;
L$^1$ is —NH—, —CH$_2$—, —NHR$^1$ or —R$^4$ with the proviso that L$^1$ is either R$^4$ or —NHR$^1$ when r is 0;
L$^2$ is —O—, —S—, —NH—, —CH$_2$—, —OR$^4$, —SR$^4$, —NHR$^1$ or —R$^4$;
Q is selected from the group consisting of proteins and peptides;
X is —R$^2$, —OR$^2$ or —CH$_2$OR$^2$;
Y is —(CHR$^3$)$_t$— with the proviso that there are no more than two OH groups; or —O—(CHR$^3$)$_u$— with the proviso that there is no more than one OH group;
wherein
R$^2$ is H, an alkyl group containing 1 to 6 carbon atoms, aryl group or an arylalkyl group;
R$^3$ is H or OH; and
R$^4$ is an alkyl group containing 1 to 6 carbon atoms, aryl group or an arylalkyl group.

5. A pharmaceutical composition, comprising a compound as claimed in claim 1 and a pharmaceutically acceptable excipient carrier.

6. A pharmaceutical composition, comprising a compound as claimed in claim 2 and a pharmaceutically acceptable excipient carrier.

7. A pharmaceutical composition, comprising a compound as claimed in claim 3 and a pharmaceutically acceptable excipient career.

8. A pharmaceutical composition, comprising a compound as claimed in claim 4 and a pharmaceutically acceptable excipient carrier.

* * * * *

UNITED STATES PATENT AND TRADEMARK OFFICE
CERTIFICATE OF CORRECTION

PATENT NO. : 5,508,387
DATED : April 16, 1996
INVENTOR(S) : Peng C. TANG et al.

It is certified that error appears in the above-indentified patent and that said Letters Patent is hereby corrected as shown below:

At column 4, line 15, before the formula, insert -- Z is --.

In the Claims:

Claim 2, column 40, line 53, delete "-CO-O;" and insert -- -CO-Q; --.

Column 6, Line 59: delete "2:50" and insert --250--.

Column 12, Line 65: delete "an" and insert --art--.

Column 34, Line 63: delete "surlfate" and insert --sulfate--.

Column 40, Line 43, Claim 2: delete "or" and insert --of--.

Column 42, lines 8-9, Claim 4: delete "$(CH_2)^n\text{-}L^2\text{-}(CH_2)_w\text{-}CO\text{-}Q$" and insert -- $L^2\text{-}(CH_2)_w\text{-}CO\text{-}Q$ --.

Signed and Sealed this

Twenty-third Day of March, 1999

Attest:

Q. TODD DICKINSON

Attesting Officer

Acting Commissioner of Patents and Trademarks